(12) United States Patent
Kaiser et al.

(10) Patent No.: US 7,967,843 B2
(45) Date of Patent: Jun. 28, 2011

(54) METHOD FOR SOFT TISSUE ATTACHMENT

(75) Inventors: Ryan A. Kaiser, Leesburg, IN (US);
Kevin T. Stone, Winona Lake, IN (US);
Troy M. Walters, Plymouth, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 127 days.

(21) Appl. No.: 12/401,261

(22) Filed: Mar. 10, 2009

(65) Prior Publication Data

US 2009/0204146 A1    Aug. 13, 2009

Related U.S. Application Data

(62) Division of application No. 10/864,900, filed on Jun. 9, 2004, now Pat. No. 7,500,983.

(51) Int. Cl.
*A61B 17/03* (2006.01)

(52) U.S. Cl. ...................................... 606/232

(58) Field of Classification Search .................. 606/151, 606/219, 228, 232
See application file for complete search history.

(56) References Cited

U.S. PATENT DOCUMENTS

| | | |
|---|---|---|
| 65,499 A | 6/1867 | Miller |
| 401,659 A | 4/1889 | Remington |
| 838,203 A | 12/1906 | Neil |
| 939,921 A | 11/1909 | Moeller |
| 1,077,006 A | 10/1913 | Smith |
| 1,340,470 A | 5/1920 | Whitmore |
| 1,386,202 A | 8/1921 | Peterson |
| 1,572,289 A | 2/1926 | Hogan |
| 2,061,385 A | 11/1936 | Nadler |
| 2,065,659 A | 12/1936 | Cullen |
| 2,121,193 A | 6/1938 | Hanicke |
| 2,242,003 A | 5/1941 | Lorenzo |
| 2,267,925 A | 12/1941 | Johnston |
| 2,329,398 A | 9/1943 | Duffy |
| 2,562,419 A | 7/1951 | Ferris |
| 2,600,395 A | 6/1952 | Domoj et al. |
| 2,665,597 A | 1/1954 | Hill |
| 2,698,986 A | 1/1955 | Brown |
| 2,883,096 A | 4/1959 | Dawson |

(Continued)

FOREIGN PATENT DOCUMENTS

DE           2529669            3/1976

(Continued)

OTHER PUBLICATIONS

"EZ Loc Femoral Fixation Device," copyright 2005 Arthrotek, Inc. (8 sheets).

(Continued)

*Primary Examiner* — Ryan J Severson
(74) *Attorney, Agent, or Firm* — Harness, Dickey

(57) ABSTRACT

An apparatus and method for fixing a selected graft relative to a selected anatomical portion. An anchor may be provided that may be interconnected with a selected graft portion that is operable to pass through a selected bore and then moved into an operable position to engage a selected portion of the bore to substantially eliminate the possibility of the graft moving in an unselected direction through the bore. In addition, a spacer member may be used to expand a selected portion of the graft to reduce localized stress and may increase ingrowth into a selected bony portion.

30 Claims, 8 Drawing Sheets

U.S. PATENT DOCUMENTS

| | | |
|---|---|---|
| 3,003,155 A | 10/1961 | Mielzynski et al. |
| 3,093,220 A | 6/1963 | Modrey |
| 3,123,077 A | 3/1964 | Alcamo |
| 3,168,850 A | 2/1965 | Tennican |
| 3,399,432 A | 9/1968 | Merser |
| 3,435,475 A | 4/1969 | Bisk |
| 3,470,834 A | 10/1969 | Bone |
| 3,500,820 A | 3/1970 | Almen |
| 3,513,484 A | 5/1970 | Hausner |
| 3,527,223 A | 9/1970 | Shein |
| 3,541,591 A | 11/1970 | Hoegerman |
| 3,664,345 A | 5/1972 | Dabbs et al. |
| 3,665,560 A | 5/1972 | Bennett et al. |
| 3,683,422 A | 8/1972 | Stemmer et al. |
| 3,695,271 A | 10/1972 | Chodorow |
| 3,699,969 A | 10/1972 | Allen |
| 3,716,058 A | 2/1973 | Tanner, Jr. |
| 3,744,488 A | 7/1973 | Cox |
| 3,845,772 A | 11/1974 | Smith |
| 3,871,368 A | 3/1975 | Johnson et al. |
| 3,875,648 A | 4/1975 | Bone |
| 3,896,500 A | 7/1975 | Rambert et al. |
| 3,910,281 A | 10/1975 | Kletschka et al. |
| 3,931,667 A | 1/1976 | Merser et al. |
| 3,943,932 A | 3/1976 | Woo |
| 3,953,896 A | 5/1976 | Treace |
| 3,976,079 A | 8/1976 | Samuels et al. |
| 3,990,619 A | 11/1976 | Russell |
| 4,006,747 A | 2/1977 | Kronenthal et al. |
| 4,013,071 A | 3/1977 | Rosenberg et al. |
| 4,085,466 A | 4/1978 | Goodfellow et al. |
| 4,149,277 A | 4/1979 | Bokros |
| 4,185,636 A | 1/1980 | Gabbay et al. |
| 4,210,148 A | 7/1980 | Stivala |
| 4,235,238 A | 11/1980 | Ogiu et al. |
| 4,243,037 A | 1/1981 | Smith |
| 4,273,117 A | 6/1981 | Neuhauser et al. |
| 4,275,717 A | 6/1981 | Bolesky |
| 4,287,807 A | 9/1981 | Pacharis et al. |
| 4,291,698 A | 9/1981 | Fuchs et al. |
| 4,301,551 A | 11/1981 | Dore et al. |
| 4,326,531 A | 4/1982 | Shimonaka et al. |
| 4,388,921 A | 6/1983 | Sutter et al. |
| 4,400,833 A | 8/1983 | Kurland |
| 4,409,974 A | 10/1983 | Freedland |
| 4,454,875 A | 6/1984 | Pratt et al. |
| 4,462,395 A | 7/1984 | Johnson |
| 4,463,753 A | 8/1984 | Gustilo |
| 4,473,102 A | 9/1984 | Ohman et al. |
| 4,493,323 A | 1/1985 | Albright et al. |
| 4,496,468 A | 1/1985 | House et al. |
| 4,532,926 A | 8/1985 | O'Holla |
| 4,537,185 A | 8/1985 | Stednitz |
| 4,573,844 A | 3/1986 | Smith |
| 4,576,608 A | 3/1986 | Homsy |
| 4,584,722 A | 4/1986 | Levy et al. |
| 4,590,928 A | 5/1986 | Hunt et al. |
| 4,602,635 A | 7/1986 | Mulhollan et al. |
| 4,605,414 A | 8/1986 | Czajka |
| 4,621,640 A | 11/1986 | Mulhollan et al. |
| 4,632,100 A | 12/1986 | Somers et al. |
| 4,649,952 A | 3/1987 | Jobe |
| 4,653,486 A | 3/1987 | Coker |
| 4,655,777 A | 4/1987 | Dunn et al. |
| 4,667,675 A | 5/1987 | Davis |
| 4,669,473 A | 6/1987 | Richards et al. |
| 4,688,561 A | 8/1987 | Reese |
| 4,690,169 A | 9/1987 | Jobe |
| 4,708,132 A | 11/1987 | Silvestrini |
| 4,719,671 A | 1/1988 | Ito et al. |
| 4,728,332 A | 3/1988 | Albrektsson et al. |
| 4,738,255 A | 4/1988 | Goble et al. |
| 4,741,330 A | 5/1988 | Hayhurst |
| 4,744,353 A | 5/1988 | McFarland |
| 4,744,793 A | 5/1988 | Parr et al. |
| 4,750,492 A | 6/1988 | Jacobs |
| 4,772,286 A | 9/1988 | Goble et al. |
| 4,773,910 A | 9/1988 | Chen et al. |
| 4,775,380 A | 10/1988 | Seedhom et al. |
| 4,776,328 A | 10/1988 | Frey et al. |
| 4,823,794 A | 4/1989 | Pierce |
| 4,828,562 A | 5/1989 | Kenna |
| 4,851,005 A | 7/1989 | Hunt et al. |
| 4,863,383 A | 9/1989 | Grafelmann et al. |
| 4,870,957 A | 10/1989 | Goble et al. |
| 4,893,619 A | 1/1990 | Dale et al. |
| 4,895,148 A | 1/1990 | Bays et al. |
| 4,896,668 A | 1/1990 | Popoff et al. |
| 4,898,156 A | 2/1990 | Gatturna et al. |
| 4,927,421 A | 5/1990 | Goble et al. |
| 4,946,468 A | 8/1990 | Li |
| 4,950,270 A | 8/1990 | Bowman et al. |
| 4,961,741 A | 10/1990 | Hayhurst |
| 4,968,315 A | 11/1990 | Gatturna |
| 4,979,956 A | 12/1990 | Silvestrini |
| 4,988,351 A | 1/1991 | Paulos et al. |
| 4,997,433 A | 3/1991 | Goble et al. |
| 5,002,550 A | 3/1991 | Li |
| 5,037,422 A | 8/1991 | Hayhurst et al. |
| 5,046,513 A | 9/1991 | Gatturna et al. |
| 5,062,344 A | 11/1991 | Gerker |
| 5,062,843 A | 11/1991 | Mahony, III |
| 5,078,731 A | 1/1992 | Hayhurst |
| 5,078,843 A | 1/1992 | Pratt |
| 5,084,050 A | 1/1992 | Draenert et al. |
| 5,092,866 A | 3/1992 | Breard et al. |
| 5,098,433 A | 3/1992 | Freedland |
| 5,100,415 A | 3/1992 | Hayhurst |
| 5,100,417 A | 3/1992 | Cerier et al. |
| 5,116,337 A | 5/1992 | Johnson |
| 5,116,373 A | 5/1992 | Jakob et al. |
| 5,116,375 A | 5/1992 | Hofmann |
| 5,127,785 A | 7/1992 | Faucher et al. |
| 5,129,902 A | 7/1992 | Goble et al. |
| 5,129,906 A | 7/1992 | Ross et al. |
| 5,139,520 A | 8/1992 | Rosenberg |
| 5,147,362 A | 9/1992 | Goble |
| 5,152,790 A | 10/1992 | Rosenberg et al. |
| 5,156,616 A | 10/1992 | Meadows et al. |
| D331,626 S | 12/1992 | Hayhurst et al. |
| 5,176,682 A | 1/1993 | Chow |
| 5,197,987 A | 3/1993 | Koch et al. |
| 5,203,787 A | 4/1993 | Nobitt et al. |
| 5,207,679 A | 5/1993 | Li |
| 5,209,753 A | 5/1993 | Biedermann et al. |
| 5,211,647 A | 5/1993 | Schmieding |
| 5,224,946 A | 7/1993 | Hayhurst et al. |
| 5,234,435 A | 8/1993 | Seagrave, Jr. |
| 5,235,461 A | 8/1993 | Kirsch et al. |
| 5,236,445 A | 8/1993 | Hayhurst et al. |
| 5,236,461 A | 8/1993 | Forte |
| 5,246,441 A | 9/1993 | Ross et al. |
| 5,258,016 A | 11/1993 | DiPoto et al. |
| 5,258,040 A | 11/1993 | Bruchman et al. |
| 5,268,001 A | 12/1993 | Nicholson et al. |
| 5,269,783 A | 12/1993 | Sander |
| 5,269,809 A | 12/1993 | Hayhurst et al. |
| 5,281,422 A | 1/1994 | Badylak et al. |
| 5,282,809 A | 2/1994 | Kammerer et al. |
| 5,282,832 A | 2/1994 | Toso et al. |
| 5,285,040 A | 2/1994 | Brandberg et al. |
| 5,290,217 A | 3/1994 | Campos |
| 5,306,301 A * | 4/1994 | Graf et al. ............... 606/232 |
| 5,320,115 A | 6/1994 | Kenna |
| 5,320,626 A | 6/1994 | Schmieding |
| 5,324,308 A | 6/1994 | Pierce |
| 5,336,240 A | 8/1994 | Metzler et al. |
| 5,356,413 A | 10/1994 | Martins et al. |
| 5,362,294 A | 11/1994 | Seitzinger |
| 5,370,661 A | 12/1994 | Branch |
| 5,370,662 A | 12/1994 | Stone et al. |
| 5,372,146 A | 12/1994 | Branch |
| 5,372,604 A | 12/1994 | Trott |
| 5,372,821 A | 12/1994 | Badylak et al. |
| 5,379,492 A | 1/1995 | Glesser |
| 5,383,878 A | 1/1995 | Roger et al. |
| 5,391,171 A | 2/1995 | Schmieding |

| Patent No. | Date | Name | | Patent No. | Date | Name |
|---|---|---|---|---|---|---|
| 5,393,302 A | 2/1995 | Clark et al. | | 5,980,559 A | 11/1999 | Bonutti |
| RE34,871 E | 3/1995 | McGuire et al. | | 6,010,525 A | 1/2000 | Bonutti et al. |
| 5,417,691 A | 5/1995 | Hayhurst | | 6,027,523 A | 2/2000 | Schmieding |
| 5,417,712 A | 5/1995 | Whittaker et al. | | 6,045,573 A | 4/2000 | Wenstrom, Jr. et al. |
| 5,423,823 A | 6/1995 | Schmieding | | 6,056,752 A * | 5/2000 | Roger ............... 623/13.12 |
| 5,423,860 A | 6/1995 | Lizardi et al. | | 6,062,344 A | 5/2000 | Okabe et al. |
| 5,425,733 A | 6/1995 | Schmieding | | 6,086,591 A | 7/2000 | Bojarski |
| 5,443,468 A | 8/1995 | Johnson | | 6,086,592 A | 7/2000 | Rosenberg et al. |
| 5,443,482 A | 8/1995 | Stone et al. | | 6,086,608 A | 7/2000 | Ek et al. |
| 5,445,833 A | 8/1995 | Badylak et al. | | 6,099,530 A * | 8/2000 | Simonian et al. ............ 606/75 |
| 5,451,203 A | 9/1995 | Lamb | | 6,099,568 A | 8/2000 | Simonian et al. |
| 5,454,811 A | 10/1995 | Huebner | | 6,132,433 A | 10/2000 | Whelan |
| 5,454,834 A * | 10/1995 | Boebel et al. ............... 606/228 | | 6,132,437 A | 10/2000 | Omurtag et al. |
| 5,456,685 A | 10/1995 | Huebner | | 6,139,565 A | 10/2000 | Stone et al. |
| 5,458,601 A | 10/1995 | Young, Jr. et al. | | 6,146,408 A | 11/2000 | Bartlett |
| 5,458,604 A | 10/1995 | Schmieding | | 6,152,928 A | 11/2000 | Wenstrom, Jr. |
| 5,464,427 A | 11/1995 | Curtis et al. | | 6,156,039 A | 12/2000 | Thal |
| 5,464,440 A | 11/1995 | Johansson et al. | | 6,159,234 A | 12/2000 | Bonutti et al. |
| 5,470,334 A | 11/1995 | Ross et al. | | 6,165,203 A | 12/2000 | Krebs |
| 5,472,452 A | 12/1995 | Trott | | 6,168,598 B1 | 1/2001 | Martello |
| 5,474,572 A | 12/1995 | Hayhurst | | 6,168,628 B1 | 1/2001 | Huebner |
| 5,480,403 A | 1/1996 | Lee et al. | | 6,187,025 B1 | 2/2001 | Machek |
| 5,486,197 A | 1/1996 | Le et al. | | 6,193,754 B1 | 2/2001 | Seedhom et al. |
| 5,500,000 A | 3/1996 | Feagin et al. | | 6,200,329 B1 | 3/2001 | Fung et al. |
| 5,520,691 A | 5/1996 | Branch | | 6,203,572 B1 | 3/2001 | Johnson et al. |
| 5,522,817 A | 6/1996 | Sander et al. | | 6,221,107 B1 | 4/2001 | Steiner et al. |
| 5,522,844 A | 6/1996 | Johnson | | 6,231,592 B1 | 5/2001 | Bonutti et al. |
| 5,522,845 A | 6/1996 | Wenstrom, Jr. | | 6,235,057 B1 | 5/2001 | Roger et al. |
| 5,524,946 A | 6/1996 | Thompson | | 6,241,747 B1 | 6/2001 | Ruff |
| 5,527,342 A | 6/1996 | Pietrzak et al. | | 6,267,766 B1 | 7/2001 | Burkhart |
| 5,540,718 A | 7/1996 | Bartlett | | 6,283,996 B1 | 9/2001 | Chervitz et al. |
| 5,549,613 A | 8/1996 | Goble et al. | | 6,296,659 B1 | 10/2001 | Foerster |
| 5,573,548 A | 11/1996 | Nazre et al. | | 6,319,271 B1 | 11/2001 | Schwartz et al. |
| 5,584,695 A | 12/1996 | Lal Sachdeva et al. | | 6,371,124 B1 | 4/2002 | Whelan |
| 5,584,835 A | 12/1996 | Greenfield | | 6,387,129 B2 | 5/2002 | Rieser et al. |
| 5,593,425 A | 1/1997 | Bonutti et al. | | 6,436,124 B1 | 8/2002 | Anderson et al. |
| 5,601,557 A | 2/1997 | Hayhurst | | 6,440,134 B1 | 8/2002 | Zaccherotti et al. |
| 5,603,716 A | 2/1997 | Morgan et al. | | 6,451,030 B2 | 9/2002 | Li et al. |
| 5,628,756 A | 5/1997 | Barker, Jr. et al. | | 6,482,210 B1 * | 11/2002 | Skiba et al. ............... 606/86 R |
| 5,628,766 A | 5/1997 | Johnson | | 6,508,830 B2 | 1/2003 | Steiner |
| 5,630,824 A | 5/1997 | Hart | | 6,511,499 B2 | 1/2003 | Schmieding et al. |
| 5,632,748 A | 5/1997 | Beck, Jr. et al. | | 6,517,578 B2 | 2/2003 | Hein et al. |
| 5,643,266 A | 7/1997 | Li | | 6,527,795 B1 | 3/2003 | Lizardi |
| 5,643,320 A | 7/1997 | Lower et al. | | 6,533,802 B2 | 3/2003 | Bojarski et al. |
| 5,643,321 A | 7/1997 | McDevitt | | 6,537,319 B2 | 3/2003 | Whelan |
| 5,645,568 A | 7/1997 | Chervitz et al. | | 6,540,750 B2 | 4/2003 | Burkhart |
| 5,645,588 A | 7/1997 | Graf et al. | | 6,544,281 B2 | 4/2003 | ElAttrache et al. |
| 5,647,874 A | 7/1997 | Hayhurst | | 6,551,343 B1 | 4/2003 | Tormala et al. |
| 5,649,963 A | 7/1997 | McDevitt | | 6,553,802 B1 | 4/2003 | Jacob et al. |
| 5,662,658 A | 9/1997 | Wenstrom, Jr. | | 6,554,862 B2 | 4/2003 | Hays et al. |
| 5,671,695 A | 9/1997 | Schroeder | | 6,579,295 B1 | 6/2003 | Supinski |
| 5,674,224 A | 10/1997 | Howell et al. | | 6,585,730 B1 | 7/2003 | Foerster |
| 5,681,352 A | 10/1997 | Clancy, III et al. | | 6,589,245 B1 | 7/2003 | Weiler et al. |
| 5,690,676 A | 11/1997 | DiPoto et al. | | 6,599,289 B1 | 7/2003 | Bojarski et al. |
| 5,699,657 A | 12/1997 | Paulson | | 6,616,694 B1 | 9/2003 | Hart |
| 5,713,005 A | 1/1998 | Proebsting | | 6,620,329 B2 | 9/2003 | Rosen et al. |
| 5,713,905 A | 2/1998 | Goble et al. | | 6,623,524 B2 | 9/2003 | Schmieding |
| 5,733,307 A | 3/1998 | Dinsdale | | 6,626,910 B1 | 9/2003 | Hugues et al. |
| 5,766,221 A | 6/1998 | Benderev et al. | | 6,626,919 B1 | 9/2003 | Swanstrom |
| 5,766,250 A | 6/1998 | Chervitz et al. | | 6,641,596 B1 | 11/2003 | Lizardi |
| 5,769,894 A | 6/1998 | Ferragamo | | 6,641,597 B2 | 11/2003 | Burkhart et al. |
| 5,782,864 A | 7/1998 | Lizardi | | 6,645,227 B2 | 11/2003 | Fallin et al. |
| 5,782,866 A | 7/1998 | Wenstrom, Jr. | | 6,652,563 B2 | 11/2003 | Dreyfuss |
| 5,785,714 A | 7/1998 | Morgan et al. | | 6,656,182 B1 | 12/2003 | Hayhurst |
| 5,810,848 A | 9/1998 | Hayhurst | | 6,682,549 B2 | 1/2004 | Bartlett |
| 5,814,070 A | 9/1998 | Borzone et al. | | 6,685,728 B2 | 2/2004 | Sinnott et al. |
| 5,824,011 A | 10/1998 | Stone et al. | | 6,689,154 B2 | 2/2004 | Bartlett |
| 5,868,789 A | 2/1999 | Huebner | | 6,692,499 B2 | 2/2004 | Tormala et al. |
| 5,885,294 A | 3/1999 | Pedlick et al. | | 6,712,849 B2 | 3/2004 | Re et al. |
| 5,899,938 A | 5/1999 | Sklar et al. | | 6,730,092 B2 | 5/2004 | Songer |
| 5,911,721 A | 6/1999 | Nicholson et al. | | 6,773,450 B2 | 8/2004 | Leung et al. |
| 5,918,604 A | 7/1999 | Whelan | | 6,780,190 B2 | 8/2004 | Maroney |
| 5,931,838 A | 8/1999 | Vito | | 6,802,862 B1 | 10/2004 | Roger et al. |
| 5,931,869 A | 8/1999 | Boucher et al. | | 6,833,005 B1 | 12/2004 | Mantas et al. |
| 5,951,559 A | 9/1999 | Burkhart | | 6,840,953 B2 | 1/2005 | Martinek |
| 5,957,953 A | 9/1999 | DiPoto et al. | | 6,863,671 B1 | 3/2005 | Strobel et al. |
| 5,964,764 A | 10/1999 | West, Jr. et al. | | 6,887,259 B2 | 5/2005 | Lizardi |
| 5,964,783 A | 10/1999 | Grafton et al. | | 6,902,573 B2 | 6/2005 | Strobel et al. |
| 5,980,558 A | 11/1999 | Wiley | | 6,916,321 B2 | 7/2005 | TenHuisen et al. |

| | | |
|---|---|---|
| 6,923,823 B1 | 8/2005 | Bartlett et al. |
| 6,923,824 B2 | 8/2005 | Morgan et al. |
| 6,972,027 B2 | 12/2005 | Fallin et al. |
| 6,986,781 B2 | 1/2006 | Smith |
| 7,097,654 B1 | 8/2006 | Freedland |
| 7,491,217 B1 | 2/2009 | Hendren et al. |
| 2001/0014825 A1 | 8/2001 | Burke et al. |
| 2001/0037131 A1 | 11/2001 | Schmieding et al. |
| 2001/0037153 A1 | 11/2001 | Rockwood et al. |
| 2001/0041937 A1 | 11/2001 | Rieser et al. |
| 2001/0041938 A1 | 11/2001 | Hein |
| 2001/0044639 A1 | 11/2001 | Levinson |
| 2001/0047206 A1 | 11/2001 | Sklar et al. |
| 2001/0053934 A1 | 12/2001 | Schmieding |
| 2002/0001964 A1 | 1/2002 | Choi |
| 2002/0004669 A1 | 1/2002 | Bartlett |
| 2002/0007182 A1 | 1/2002 | Kim |
| 2002/0010513 A1 | 1/2002 | Schmieding |
| 2002/0013608 A1 | 1/2002 | ElAttrache et al. |
| 2002/0099411 A1 | 7/2002 | Bartlett |
| 2002/0111653 A1 | 8/2002 | Foerster |
| 2002/0120292 A1 | 8/2002 | Morgan |
| 2002/0128684 A1 | 9/2002 | Foerster |
| 2002/0147463 A1 | 10/2002 | Martinek |
| 2002/0161401 A1 | 10/2002 | Steiner |
| 2002/0161439 A1 | 10/2002 | Strobel et al. |
| 2002/0173788 A1 | 11/2002 | Bojarski et al. |
| 2002/0188298 A1 | 12/2002 | Chan |
| 2003/0023268 A1 | 1/2003 | Lizardi |
| 2003/0088272 A1 | 5/2003 | Smith |
| 2003/0120309 A1 | 6/2003 | Colleran et al. |
| 2003/0130694 A1 | 7/2003 | Bojarski et al. |
| 2003/0135239 A1 | 7/2003 | Gabriel et al. |
| 2003/0135963 A1 | 7/2003 | Holbrook et al. |
| 2003/0167072 A1 | 9/2003 | Oberlander |
| 2003/0167090 A1 | 9/2003 | Chervitz et al. |
| 2003/0176865 A1 | 9/2003 | Supinski |
| 2003/0176919 A1 | 9/2003 | Schmieding |
| 2004/0015171 A1 | 1/2004 | Bojarski et al. |
| 2004/0092936 A1 | 5/2004 | Miller et al. |
| 2004/0098051 A1 | 5/2004 | Fallin et al. |
| 2004/0138706 A1 | 7/2004 | Abrams et al. |
| 2004/0147929 A1 | 7/2004 | Biedermann et al. |
| 2004/0153153 A1 | 8/2004 | Elson et al. |
| 2004/0162579 A1 | 8/2004 | Foerster |
| 2004/0243178 A1 | 12/2004 | Haut et al. |
| 2005/0038426 A1 | 2/2005 | Chan |
| 2005/0096696 A1 | 5/2005 | Forsberg |
| 2005/0096697 A1 | 5/2005 | Forsberg et al. |
| 2005/0107828 A1 | 5/2005 | Reese |
| 2005/0119531 A1 | 6/2005 | Sharratt |
| 2005/0222618 A1 | 10/2005 | Dreyfuss et al. |
| 2005/0222619 A1 | 10/2005 | Dreyfuss et al. |
| 2005/0267479 A1 | 12/2005 | Morgan et al. |
| 2005/0277961 A1 | 12/2005 | Stone et al. |
| 2005/0283156 A1 | 12/2005 | Schmieding et al. |
| 2005/0283158 A1 | 12/2005 | West |
| 2006/0079904 A1 | 4/2006 | Thal |
| 2007/0016305 A1 | 1/2007 | Chudik |
| 2007/0049944 A1 | 3/2007 | Stone et al. |
| 2007/0225719 A1 | 9/2007 | Stone et al. |
| 2008/0161852 A1 | 7/2008 | Kaiser et al. |

FOREIGN PATENT DOCUMENTS

| | | |
|---|---|---|
| DE | 2747312 | 4/1979 |
| DE | 2818254 | 10/1979 |
| DE | 4127550 | 2/1993 |
| EP | 0129442 | 12/1984 |
| EP | 0172130 | 2/1986 |
| EP | 0241240 | 10/1987 |
| EP | 0241792 | 10/1987 |
| EP | 0260970 | 3/1988 |
| EP | 0270704 | 6/1988 |
| EP | 0282789 | 9/1988 |
| EP | 0317406 | 5/1989 |
| EP | 0340159 | 11/1989 |
| EP | 0346183 | 12/1989 |
| EP | 0349173 | 1/1990 |
| EP | 0374088 | 6/1990 |
| EP | 0409364 | 1/1991 |
| EP | 0415915 | 3/1991 |
| EP | 0451932 | 10/1991 |
| EP | 0464480 | 1/1992 |
| EP | 0497079 | 8/1992 |
| EP | 0502509 | 9/1992 |
| EP | 520177 | 12/1992 |
| EP | 0520177 | 12/1992 |
| EP | 0546726 | 6/1993 |
| EP | 0574707 | 12/1993 |
| EP | 0582514 | 2/1994 |
| EP | 0591991 | 4/1994 |
| EP | 0627203 | 12/1994 |
| FR | 2622790 | 5/1989 |
| FR | 2655840 | 6/1991 |
| FR | 2682867 | 4/1993 |
| FR | 2687911 | 9/1993 |
| FR | 2688689 | 9/1993 |
| FR | 2704140 | 10/1994 |
| GB | 1413477 | 11/1975 |
| GB | 1485681 | 9/1977 |
| GB | 2118474 | 11/1983 |
| GB | 2227175 | 7/1990 |
| GB | 2253147 | 9/1992 |
| JP | 5300917 | 11/1993 |
| WO | WO-8603666 | 7/1986 |
| WO | WO-8901767 | 3/1989 |
| WO | WO-8909030 | 10/1989 |
| WO | WO-8910096 | 11/1989 |
| WO | WO-9008510 | 8/1990 |
| WO | WO-9203980 | 3/1992 |
| WO | WO-9314705 | 8/1993 |
| WO | WO-9529637 | 11/1995 |
| WO | WO-9532670 | 12/1995 |
| WO | WO-9629029 | 9/1996 |
| WO | WO-9812991 | 4/1998 |
| WO | WO-9812992 | 4/1998 |

OTHER PUBLICATIONS

"SE Graft Tensioning System Surgical Technique," Linvatec Corporation copyright 2003, 2004.

"Technique for ACL Reconstruction with Acufex Director Drill Guide and Endobutton CL," by Thomas D. Roseberg, copyright 1999 Smith & Nephew.

Bio-Intrafix (TCP/PLA & Intrafix, Tibial Soft Tissue Fasteners, by DePuy Mitek, 6 sheets, (date unknown).

* cited by examiner

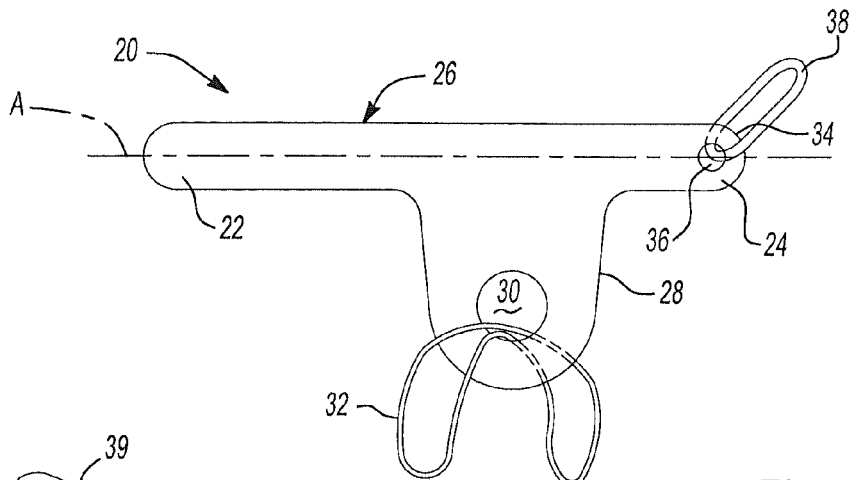
*Figure-1A*
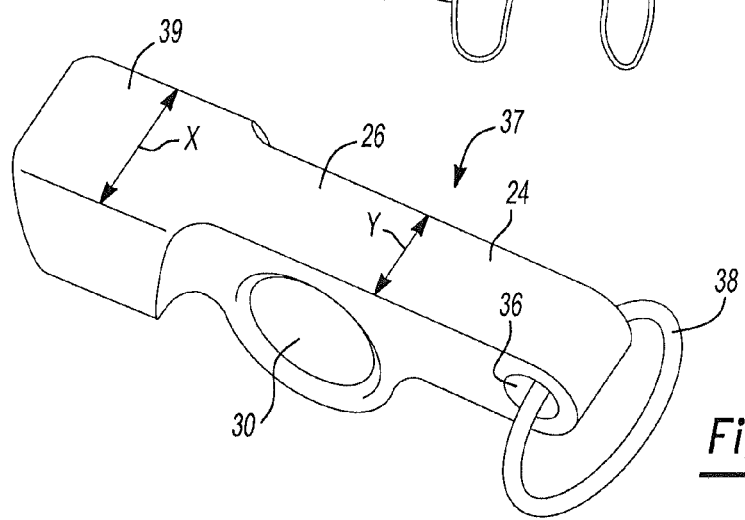
*Figure-1B*
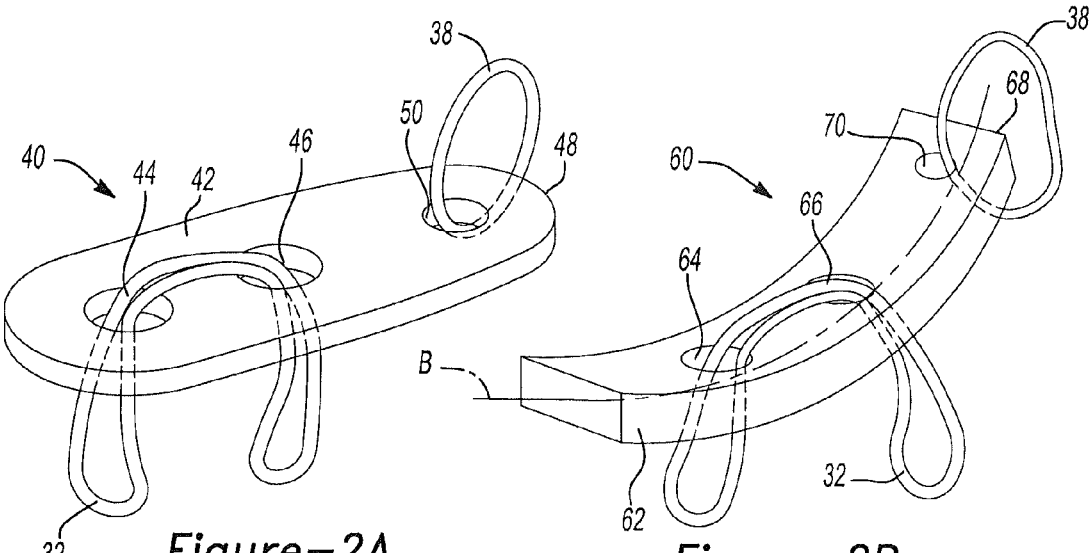
*Figure-2A*     *Figure-2B*

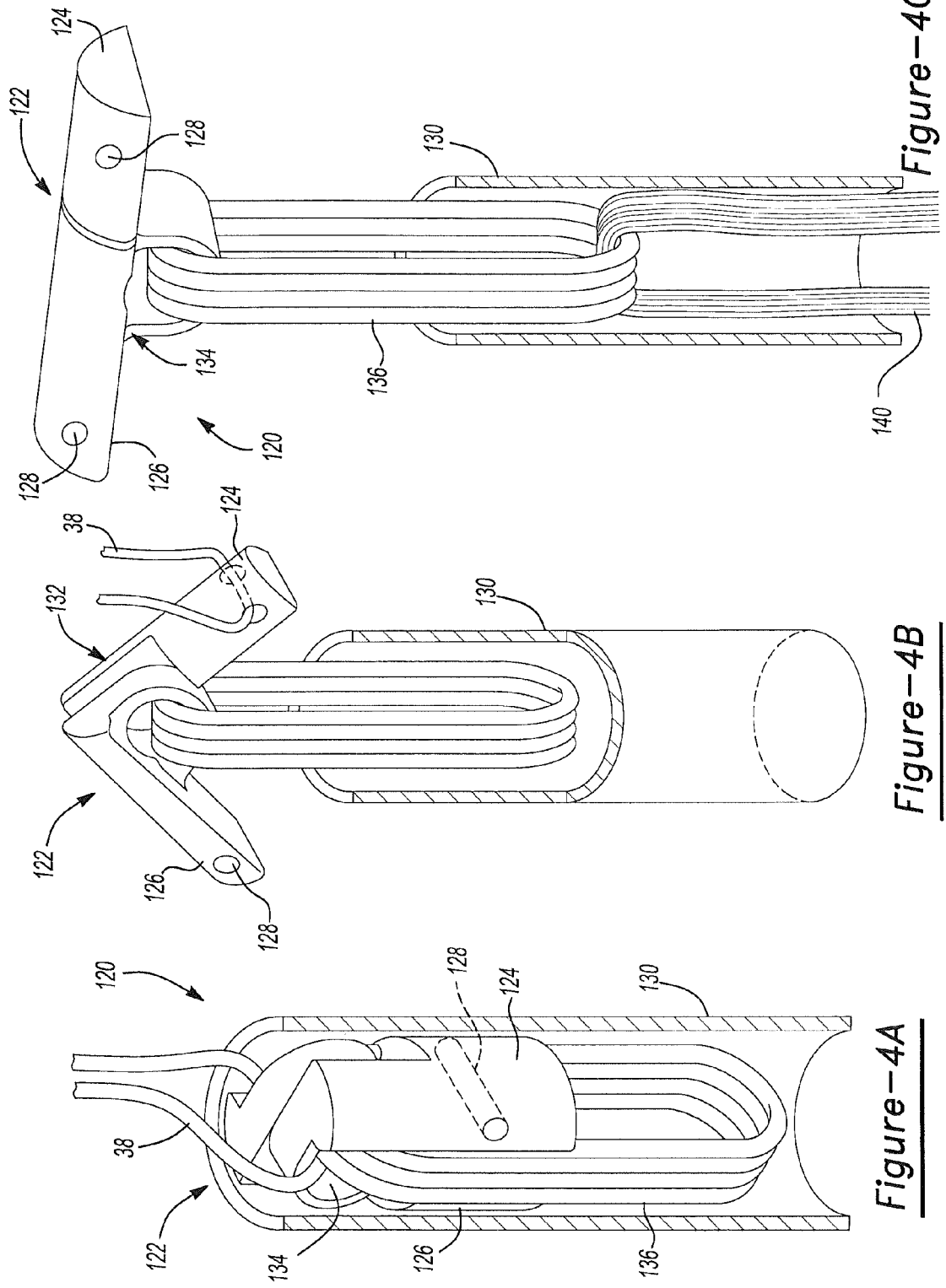

METHOD FOR SOFT TISSUE ATTACHMENT

CROSS-REFERENCE TO RELATED APPLICATIONS

This application is a divisional of U.S. patent application Ser. No. 10/864,900 filed on Jun. 9, 2004, which issued as U.S. Pat No. 7,500,983 on Mar. 10, 2009. The entire disclosure of the above application is incorporated herein by reference.

FIELD

The present application relates generally to orthopedic procedures; and relates particularly to orthopedic procedures for interconnecting soft tissue to a bony portion of an anatomy.

BACKGROUND

In an anatomy, such as a human anatomy, various soft tissue portions are interconnected with various bony portions. For example, a tendon may interconnect a selected muscle group with a selected portion of the anatomy. Similarly, a ligament may interconnect two bony portions. For example, the anterior cruciate ligament interconnects a portion of the tibia with a portion of the femur. Although the natural and healthy anatomy generally is able to support the various portions of the anatomy with the natural ligaments and tendons, and other selected soft tissues, injury, age, or other circumstances may cause the weakening or breaking of various soft tissue portions.

For example, a strain, other injury, or disease may weaken various soft tissue portions, such as the anterior cruciate ligament (ACL). The breaking or weakening of the tissue may require the tissue to be reconnected or replaced with various autografts or xenografts that may be made of natural or synthetic materials. These various materials are generally interconnected with selected portions of the anatomy using screws or other similar friction or obstruction holding devices.

Though various procedures and instruments may allow for interconnection of soft tissue with selected bony portions, it may be desirable to perform a procedure substantially percutaneously or through a small incision or in less time. Generally, the screws or the obstruction devices must be driven into the selected bony portion to hold the selected soft tissue in the appropriate location. The procedure must be planned and executed in a particular manner to insure that appropriate fixation of the soft tissue to the selected bony portion. Therefore, it may be desirable to provide an instrument and method that allows for a substantially quick implantation or connection of a selected soft tissue graft or soft tissue portion to a selected bony portion.

SUMMARY

A device for connecting or holding a soft tissue graft relative to a selected anatomicat portion such as a bone portion. An anchor may be provided that is operably interconnected with a selected portion of the graft and the anchor may anchor the connection portion to the selected bony portion. For example, the anchor portion may be passed through a bore and manipulated to hold the soft tissue graft relative to the bore by providing an interference fit with a portion of the bone next to or relative to the bore. The anchor may be formed as substantially a single piece or may be an assembly of a plurality of pieces, such that the anchor may pass through the bore and may be manipulated to interfere with passing in an opposite direction through the bore again.

In addition, a portion of the instrument or fixation device may include a spreading or spacer portion that may hold apart selected portions of a selected graft during an implant procedure and after the implantation has occurred. The spacer may allow a reduction of a local stress on a selected implant after implantation and may ease implanting of the implant. In addition, a spacer may allow for proper positioning of various portions of the implant during the procedure and insure that the implant is kept at a proper spacing after implantation. Moreover, a spacer may assist in allowing for natural adhesion to selected portions of the anatomy.

According to various embodiments a single piece anchor member to selectively anchor a graft relative to a selected portion of an anatomy includes a lever arm extending along a first axis between a first end and a second end. The lever arm includes a connection region extending from the lever arm and an activation region defined by the lever arm. The lever arm is selectable between an activated position and a non-activated position with the activation region. The activated position selectively holds the graft relative to the selected portion of the anatomy.

According to various embodiments a method of fixing a graft in a selected region of an anatomy with an anchor member includes forming a bore in the selected region of the anatomy thereby defining an interior surface within the bore and an exterior surface outside of the bore. The graft may be associated with the anchor member and passed with the anchor member through a selected portion of the bore to a first position in a first orientation. The anchor member may be moved to a second position thereby selectively engaging the exterior surface.

According to various embodiments a graft implant kit to interconnect a graft and a selected portion of an anatomy is disclosed. The kit includes an anchor selectable between an activated position and a non-activated position. An anchor passing member extending from the anchor to move the anchor between the activated position and the non-activated position. A spacer may extend from the anchor member. The spacer lays between selected portions of the graft to decrease a local stress in the graft.

Further areas of applicability will become apparent from the detailed description provided hereinafter. It should be understood that the detailed description and various embodiments are intended for purposes of illustration only and are not intended to limit the scope of the teachings.

BRIEF DESCRIPTION OF THE DRAWINGS

The present description and appended claims will become more fully understood from the detailed description and the accompanying drawings, wherein:

FIG. 1A is a side plan view of an anchor according to various embodiments;

FIG. 1B is a perspective view of an anchor according to various embodiments;

FIG. 2A is a top perspective view of an anchor according to various embodiments;

FIG. 2B is a top perspective view of an anchor according to various embodiments;

FIG. 4A is an anchor assembly according to various embodiments in an unactivated position;

FIG. 4B is the anchor of FIG. 4A in a partially activated position;

FIG. 4C is the anchor of FIG. 4A in an activated position;

DETAILED DESCRIPTION OF VARIOUS EMBODIMENTS

Figure 3A:
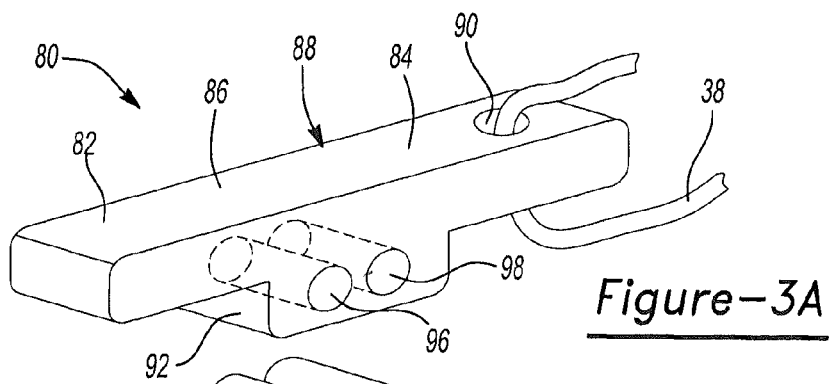
FIG. 3A is an exploded view of an anchor according to various embodiments.

The following description of various embodiments is merely exemplary in nature and is in no way intended to limit the invention, its application, or uses. Although the following description may relate to providing a soft tissue anchor relative to a femur, such as for an anterior cruciate ligament (ACL) fixation, the various apparati and methods may be used for a plurality of procedures. For example, the various instruments may be used to affix or hold a hamstring, Achilles tendon allograft, other soft tissue, or any other appropriate portion. In addition, although various embodiments may be illustrated to be interconnected with a selected graft using a flexible strand, such as a suture, it will be understood that a graft may be affixed directly to an implant member. Therefore, it will be understood that the following description is merely exemplary of various embodiments and is not intended to be limiting.

With reference to FIG. 1A, an anchor 20 may be provided. The anchor 20, according to various embodiments, may be used to anchor any appropriate portion such as a soft tissue, suture, or the like. The anchor 20 may include a first flange or portion 22 extending in a first direction and a second flange or portion 24 extending in a second direction. The first flange 22 and the second flange 24 generally interconnect to form a lever or arm portion 26 of the anchor 20. The arm portion 26, as described further herein, may be maneuvered to engage a selected portion of an anatomy to hold a selected graft or portion relative to the anatomy.

Extending from the arm portion 26 is a holding or engaging portion 28. The engaging portion 28 may be positioned relative to the arm portion 26 in any appropriate manner. For example, the first flange 22 may have a length that is greater than the second flange 24, therefore, the soft tissue anchor portion 28 may be formed closer to a selected end than another selected end of the anchor 20.

The engaging portion 28 may also include a fixation area or portion 30. The fixation portion 30 may be a bore or passage provided through the soft tissue anchor portion 28. The passage 30 may allow a selected portion of a soft tissue graft, or any other appropriate implant to pass through. Alternatively, a suture or strand portion 32, such as a loop, a plurality of loops, or a link may pass through the passage 30 to engage the anchor 20 and interconnect the soft tissue graft or portion. Therefore, the suture loop 32 that may be a substantially continuous suture loop, may be provided through the passage 30.

The lever arm 26 of the anchor 20 may also be formed in any appropriate manner. For example, the lever arm 26 may extend substantially along a selected axis A and be substantially planar. Alternatively, the lever arm 26 may extend along any appropriate radius to define a substantially curved lever arm portion. It will be understood, therefore, that the lever arm portion 26 may be formed in any appropriate manner for selected applications.

An engagement or activation area 34 may extend from a portion of the first flange 22 or the second flange 24. The activation area may include a passageway 36 that may be formed in the portion of the second flange 24. An activation or passing member, such as a suture portion 38, may also pass through the activation bore 36 to assist in positioning the anchor 20. The suture portion 38 will be understood to be any appropriate portion, such as any appropriate flexible strand suture portion, or may also include a rigid member to interconnect with the activation portion of the anchor 20. Nevertheless, the suture portion 38 may be passed through a selected portion of anatomy to move the anchor 20 through the selected portion of the anatomy, as described in detail herein. It will also be understood that the suture portion 38 may not be necessary and the anchor 20 may include a portion that may act as a portion to pull the anchor 20 through a selected portion of the anatomy. For example, a generally integrally formed portion may extend from the anchor 20 and near the activation region 30 that may or may not be frangible and may be detached from the anchor 20 at a selected time. Therefore, the suture portion 38 may not be necessary and may be omitted in lieu of providing another portion that may add to move the anchor 20 in a selected fashion.

With reference to FIG. 1B, an anchor 37, according to various embodiments, is illustrated. The anchor 37 may be similar to the anchor 20 and similar numerals are used to reference similar portions. For example, the anchor 37 may include a first flange portion 39 that includes at least a first dimension X greater than a dimension Y of the second flange 24. As discussed above, the first flange 39 and the second flange portion 24 may define a lever or arm portion 26. Defining at least a portion of the lever arm portion 26 is the fixation portion 30. The fixation portion 30 may include a dimension that at least is partly defined by the lever arm 26. Although a portion of the fixation portion 30 may extend beyond the arm 26, the arm 26 may define at least a portion of the fixation portion 30. In addition, an activation portion or bore 36 may be defined by a portion of the arm 26, such as a portion of the second flange 24. As discussed above, an activation member 38 may be provided to activate the anchor 37 at an appropriate time.

With reference to FIG. 2A, an anchor 40 according to various embodiments may be provided that generally includes a planar body or portion 42. Formed through the body 42 may be a soft tissue anchor portion that may include a first bore 44 and a second bore 46. The soft tissue graft or a selected portion, such as a suture loop 32, may be provided through the bores 44, 46 to engage a selected soft tissue portion. In addition, the anchor 40 may include a activation region 48 that may include a activation bore 50, similar to the activation bore 36 of the anchor 20. Similarly, the suture 38 or other appropriate portion may extend through the activation bore 50 to assist in passing the anchor 40 through a selected portion and manipulating the anchor 40 in a selected manner. Therefore, the anchor 40 may be provided, such that it will pass through a selected portion of the anatomy, as described further herein, and manipulated with the suture loop 38 to assist in fixing a selected soft tissue graft with the anchor 40.

With reference to FIG. 2B, an anchor 60 may be provided including a substantially arcuate body portion 62 that extends along an arc B of any selected radius. Similar to the anchor 40, the anchor 60 may include a soft tissue attachment portion, including a first bore 64 and a second bore 66. The suture strand or loop 32 may pass through the bores 64, 66 to engage a portion of soft tissue or a portion of soft tissue may engage the bore 64, 66. Nevertheless, the anchor 60 may be used to fix a selected portion of soft tissue relative to a portion of anatomy, or any other appropriate purpose.

The anchor 60 may also include a activation region 68 that may define a activation bore 70, similar to the bore 50 of the anchor 40. Again, similar to the anchor 40, the suture loop 38 may be passed through the bore 70 to be used to manipulate the anchor 60 in a selected manner during a procedure. Nevertheless, according to various embodiments, a portion may extend from the anchor 60 that is not necessarily included as a suture loop 38. Therefore, it will be understood that providing the suture loop 38 is merely exemplary.

Further, it will be understood that an anchor need not be formed as a single member. In addition to being formed as a single member, the anchor may be formed to include any appropriate geometry, shape, size, or the like. Therefore, the anchor need not include simply straight or curved portions or include a portion that extends from a portion of the anchor to engage the implant, but may be formed in any appropriate manner. It will be understood that the anchor may be passed through a selected portion of the anatomy in a first manner or condition and then manipulated to a second manner or position to assist in positioning the anchor in a selected position to perform the necessary tasks.

Figure 3B:
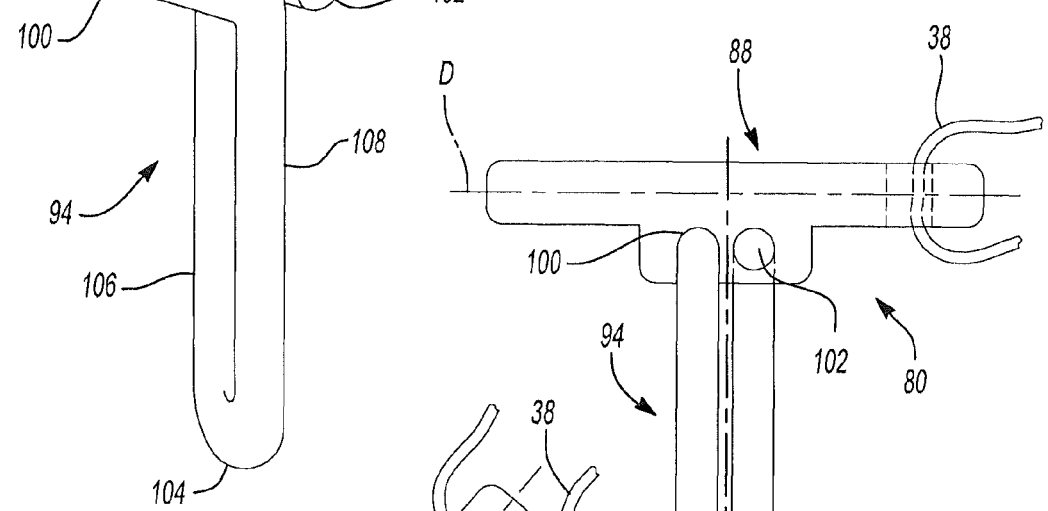
FIG. 3B is an assembled view of the anchor of FIG. 3A in an activated position.
Figure 3C:
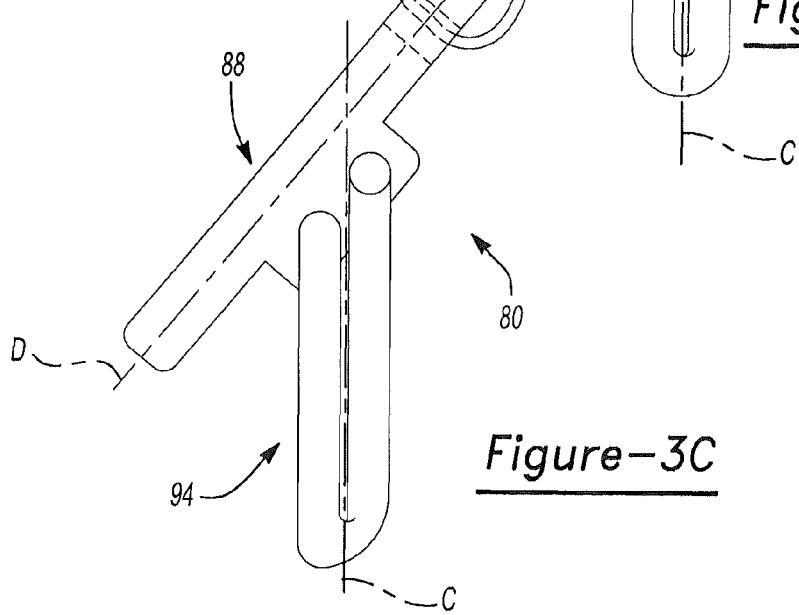
FIG. 3C is an elevational view of the anchor of FIG. 3A in an activated position.

With reference to FIGS. 3A-3C, an anchor 80 according to various embodiments is illustrated. The anchor 80 may include a first flange or portion 82 extending in a first direction and second flange or portion 84 extending in a second direction from a central region 86. The arms 82 and 84 define a activation portion or member 88 of the anchor 80 as discussed herein. The lever arm portion 88 may be maneuvered, as discussed herein, to engage a selected portion of anatomy to hold a graft or other portion relative to a selected portion of the anatomy.

Formed in the second arm portion 84 is a activation bore 90 through which the activation suture 38 may be passed. As described herein, the activation suture 38 may be used to position the anchor 80 in a selected position and manipulate or maneuver the anchor from an unactivated to an activated position, thereby allowing the lever arm portion 88 to abut a selected portion of the anatomy and hold the anchor 80 in a selected position.

Defined near the fulcrum or central area 86 is an engaging portion 92. The engaging portion 92 may engage a graft engaging member or portion 94. The graft engaging portion 94 may be formed of a selected material, as described herein. The engaging region 92 may include a first bore 96 and a second bore 98. The bores 96, 98 may engage selected portions of the graft engaging section 94 such as first region 100 and a second region 102.

The graft engaging member 94 generally defines a substantially U or curved portion 104 from which extends a first extending portion 106 and a second extending portion 108. The first extending portion 106 extends to the first engaging member 102 while the second engaging portion 108 extends to the first engaging portion 100. Each of the engaging portions 100, 102 may engage a selected one of the bore 96, 98.

With particular reference to FIG. 3B, in an activated or neutral position, the anchor 80 includes the lever arm 88 at a generally perpendicular position relative to the graft engaging portion 94. The graft engaging portion 94 may define an axis C that is generally perpendicular to an axis D of the lever arm 88. Therefore, in the neutral or unactivated position, the lever arm 88 does not position or apply a substantial amount of stress to the graft engaging portion 94. As illustrated, a first engaging portion 100 and a second engaging portion 102 are passed through or engage a selected one of the bores 96, 98. In this way, the lever arm 88 is interconnected with the graft engaging portion 94 by both of the engaging portions 100, 102 of the graft engaging portion 94.

With particular reference to FIG. 3C, in an activated position, the activation suture 38 may apply a force to the lever arm 88 such that the lever arm 88 may be positioned or moved to an angle relative to the graft engaging portion 94. The axis D of the lever arm is generally positioned at an angle having an internal angle of less than 90° relative to the axis C of the graft engaging portion. In this way, a distance or width defined by the anchor 80 is less than the length of the lever 88 to allow for the anchor 80 to be passed through a selected portion of the anatomy.

The graft engaging member 94 may be formed of any selected material that may be moved from a first position to a second position and allowed to regain its first position or orientation substantially after the removal of a selected force. For example, the graft engaging member 94 may be formed of a wire of a selected material, such as a shape memory material including the material known as NITINOL™. It will be understood, however, that a shape memory material may be any appropriate material that may include a first shape, be deformed to a second, and substantially re-obtain the first shape. Therefore, shape memory materials may include, but are not limited to, metals, metal alloys, polymers, strands, natural and synthetic materials, or the like. The shape memory material may include a first selected shape or orientation which is generally maintained by the material and may be returned to or maintained by the material after deforming the material to a second shape or orientation.

As illustrated in FIG. 3C, the activation arm 88 may disorientate or move the graft engaging portion 94 into a second portion while the graft engaging portion 94 may re-obtain its first orientation, just as that illustrated in FIG. 3B, after the activation arm 88 has been released. Therefore, the graft, as discussed herein, may be held relative to a selected portion of the anatomy with the anchor 80 without substantially binding the graft in the graft engaging portion 94. The graft engaging portion 94 may be any appropriate substance such as a wire, plastic thread, filament, suture, or the like.

With reference to FIGS. 4A-4C, an anchor 120 according to various embodiments is illustrated. The anchor 120 may include an activation or lever portion 122 that generally includes a first arm portion 124 and a second arm portion 126. Defined in either the first or second arm portion, and illustrated in the first arm portion 124, is an activation bore 128 that may be formed in any appropriate orientation through either of the first arm position 124 or the second arm position 126. The activation bore 128 may be interconnected with the activation suture 38. Alternatively, the activation suture 38 may be positioned relative to any portion of the anchor 120. For example, the activation suture 38 may be interconnected with a sleeve 130 that substantially surrounds the lever arm 120. The lever portion 122 generally includes a central axle or rotation area about which the first arm 124 and the second arm 126 may rotate.

With particular reference to FIG. 4B, and described further herein, the first arm 124 may rotate about the axle area 132 relative to the second arm 126. This may allow the lever arm portion 122 to be moved from an unactivated to an activated position and allow it to selectively engage a selected portion of the anatomy. The axle portion 132 may be formed in any appropriate manner. For example, a portion of the first arm 124 may extend into a portion of the second arm 126 yet be substantially movable relative thereto. Therefore, the arm portions 124, 126 define an integral axial portion thereby not requiring a separate axle member. Nevertheless, it will be understood that an axle member may be provided in both the first arm and the second arm 124, 126 so that the arms 124, 126 may rotate relative to the axle portion to allow for movement of the first arm 124 relative to the second arm 126.

Nevertheless, a bore or opening 134 may be provided between the first arm 124 and the second arm 126 generally near the axle region 132 to allow for the passing of a suture 136 or similar apparatus. The suture 136 may allow a graft to be engaged by the anchor 120 to be held by the anchor in a selected position.

During insertion of the anchor 120, the activation member 122 and the suture loops 136 may be positioned within a sleeve or tube 130. It will be understood that the sleeve 130 is not necessary to position the anchor 120 but might be provided for various reasons such as positioning the graft, positioning the anchor and other appropriate reasons relative to the selected portions of the anatomy.

Nevertheless, as the anchor 120 is passed through a selected portion of the anatomy, the sleeve 130 may be stopped according to appropriate means in a selected area. Therefore, as illustrated in FIG. 4B, as the lever portion 122 is moved between an unactivated and an activated position, the lever 122 is substantially removed from the sleeve 130. This allows the first arm 124 to move relative to the second arm member 126 and vice versa while being substantially free of the obstruction of the sleeve 130. Nevertheless, also during moving the anchor 120 into a selected position, the sleeve 130 may assist in holding the arm portions 124, 126 of the lever portion 122 in a selected orientation.

With reference to FIG. 4C, once the anchor 120 including the lever arm 122 are positioned in a selected orientation, the lever portion 122 is in a substantially activated position such that the first arm 124 is substantially aligned and in a single axis with a second lever arm 126. As discussed above, this may be performed by substantially rotating about a central axle area 130, the first arm 124 relative to the second arm 126 and vice versa. The suture portion 136 extends from the lever portion 122 and may be positioned within the sleeve 130. A graft 140 that may be positioned over the suture member 136 may also extend through a portion of the sleeve 130 for positioning the graft 140 in a selected orientation. This allows the anchor 120 to be positioned in a selected portion of the anatomy and manipulated from the unactivated position to the activated position, particularly shown in FIG. 4C.

Figure 5A:
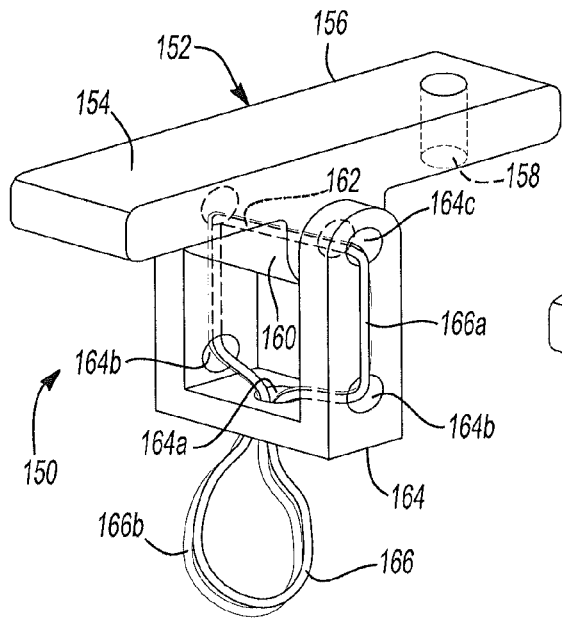
FIG. 5A is a perspective view of an anchor according to various embodiments.

With reference to FIG. 5A, an anchor 150, according to various embodiments, may include a activation portion 152 that includes a first arm portion 154 and a second arm portion 156. Defined in a selected arm portion, such as the second arm portion 156, may be a activation bore 158. As discussed above, an appropriate member, such as the activation suture 38, may be passed through the activation bore 158 to move the activation or lever section 152 from a first position or unactivated position to an activated position. The lever arm 152 defines a central or fulcrum region 160 that includes a bore 162. Further, an extension member 164 may be interconnected with the bore 162 or the fulcrum region 160 with a selected suture member 166.

A suture member 166 may pass through a first or central bore 164A defined in a selected region of the extension member 164 and through a second set of bores 164b and again through a third set of bores 164c. Therefore, the suture member 166 may define a substantially figure "8" portion 166a that includes a first portion of the figure "8" 166a that substantially interconnects the lever arm 152 with the extension member 164. A second section of the suture portion 166b may be used to engage a selected graft portion for positioning relative to a selected portion of the anatomy. As discussed herein, the lever arm 152 may be moved to a selected portion of the anatomy in an unactivated position and moved to the activated position, substantially illustrated in FIG. 5A, to engage a selected portion of the anatomy. The first section of the suture portion 166a allows for the lever arm 152 to move relative to the extension member 164 and the graft extending from the second portion of the suture 166b.

Figure 5B:
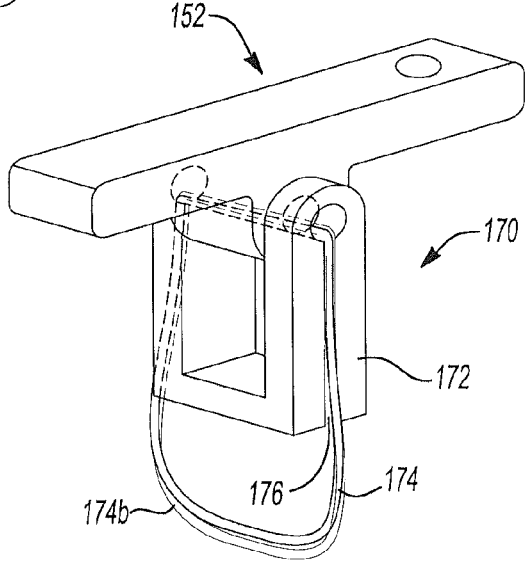
FIG. 5B is a perspective of an anchor according to various embodiments.

With reference to FIG. 5B, an anchor portion 170 includes a lever portion 152 substantially similar to the lever portion 152 illustrated in FIG. 5A, and will not be described in great detail here. Nevertheless, an extension member 172 extends from the lever arm portion 152 and is interconnected therewith with a suture portion 174. The suture portion defines substantially a continuous loop that includes a portion that extends through a bore defined in the extension member 172 and the fulcrum bore defined by the lever arm 152. A second section of the suture 174B extends and may engage a selected graft for implantation. As discussed above, a activation suture or portion may be used to pass the anchor 170 through a selected portion of the anatomy and used to move the lever arm 152 from an inactivated to an activated position. The suture 174 may be positioned in a groove or detent 176 to substantially limit an abrasion between the suture 174 and a portion of the anatomy.

Figure 6A:
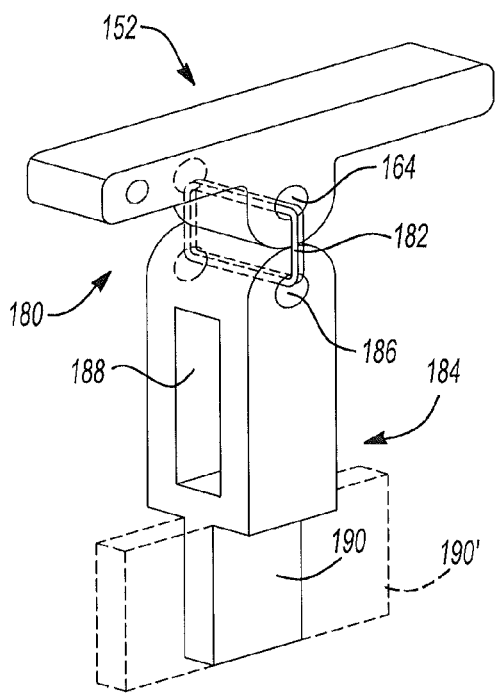
FIG. 6A is a perspective view of an anchor according to various embodiments.

With reference to FIG. 6A, an anchor assembly 180 according to various embodiments is illustrated. The anchor assembly 180 may include the lever arm 152 substantially similar to the lever arm 152 discussed above. A suture member 182 may be provided to interconnect the lever arm 152 with a spacer or extension member 184. The extension member 184 may define a bore 186 that allows the suture 182 to pass through and engage the bore 164 defined by the lever portion 152.

A selected graft may be passed through an opening or passage 188 defined by the extension spacer member 184 and allowed to drape through the opening 188 and over a spacer portion 190 of the extender spacer 184. The spacer portion 190 may be provided in any appropriate size, dimension, geometry, or the like. For example, as illustrated in phantom in FIG. 6A, the spacer portion 190' may extend a distance beyond a dimension of the spacer member 184 otherwise defined by the portion including the opening 188. It will be understood that the spacer portion 190 may also be provided in any appropriate geometry to interact with the anchor 152 or a portion, such as a soft tissue portion, passed through the opening 188. Therefore, as discussed herein, stress on a particular area of the graft may be reduced and the spacer 190 may be used to position the graft adjacent a selected portion of the anatomy. Nevertheless, the interconnection suture 182 between the lever portion 152 and the extension spacer 184 may allow for the lever arm 182 to be moved relative to the extension spacer portion 184 such as with a activation suture or portion.

Figure 6B:
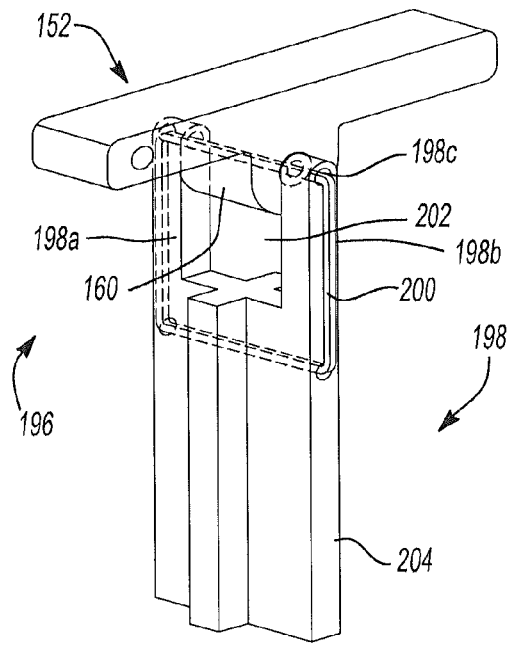
FIG. 6B is a perspective view of an anchor according to various embodiments

With reference to FIG. 6B, an anchor 196, according to various embodiments, is illustrated. The anchor assembly 196 may include the lever portion 152, as discussed above. The anchor assembly 196 also includes a spacer extender portion 198 that may be interconnected with the lever portion 152 using a connection suture 200 or other appropriate mechanisms. The extender portion 198 includes a first arm 198A and a second arm 198B that may extend around a selected portion, such as the central or fulcrum region 160 of the lever portion 152 to allow the attachment suture 200 to interconnect the lever portion 152 and the spacer portion 198. The connection suture 200 may form a substantially continuous loop that passes through a plurality of bores defined by the spacer extender portion 198 to interconnect the lever portion 152 and the spacer portion 198.

Defined between the lever portion 152 and the spacer portion 198 is an opening or passage 202. The passage 202 may allow for positioning of a graft relative to the anchor assembly 196. The graft may drape through the opening 202 and be held in a relative position with the spacer portion 204 of the spacer extension portion 198. As discussed above and herein, the spacer portion may allow for positioning the graft in a selected position and substantially reducing a localized stress on the graft assembly.

As discussed above, the spacer extension portion 198 may include the spacer portion 204 formed in any appropriate shape, size, geometry, or the like. Therefore, as exemplary illustrated, the spacer portion 204 may be substantially cruciform in shape. The cruciform shape may extend and define a portion of the opening 202 or may extend only a portion of the length of the spacer portion 204. Therefore, it will be understood that the spacer portion 204 may be any appropriate shape, size, geometry, or other appropriate condition based upon selected parameters.

Figure 7A:
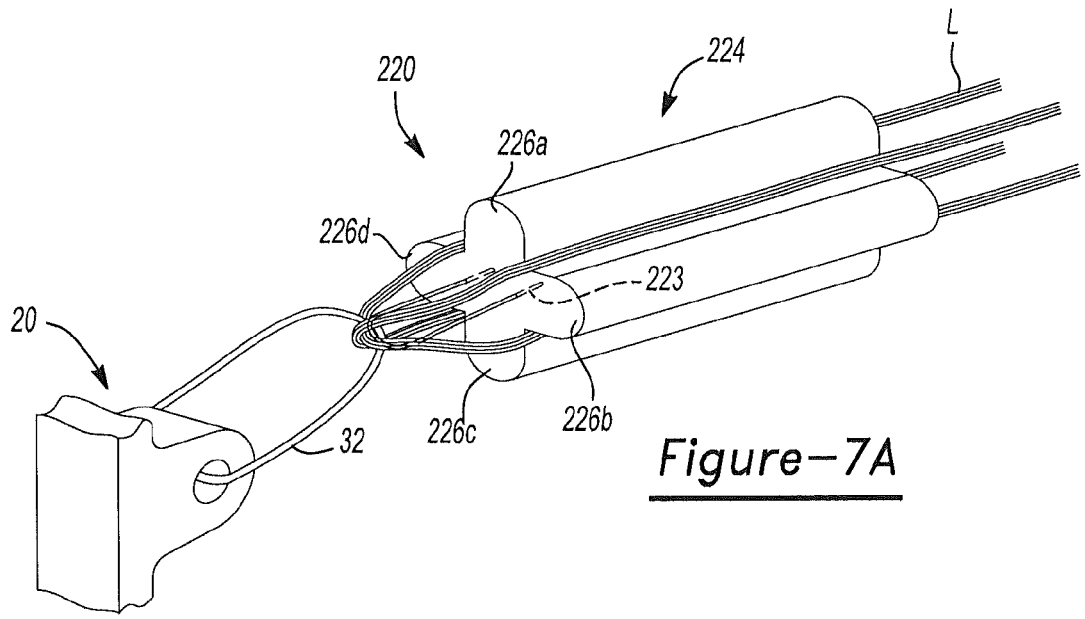
FIG. 7A-7C are top perspective views of spacers according to various embodiments.

With reference to FIG. 7A, a spacer or separator 220 is illustrated. The spacer 220 may be interconnected with the anchor 20, or any appropriate anchor or mechanism, with a connection loop or portion 222. The spacer 220 includes a spacer body 224 that may define a plurality of sections to assist in separating and spacing a portion of a soft tissue graft. For example, the body may define a plurality of ridges 226A, 226B, 226C, and 226D. The various ridges assist in holding portions of ligament implants, or other appropriate implants, apart for a selected period of time. For example, a plurality of strands of a soft tissue or graft, such as a ligament L, may be looped through the connecting suture 32 and allowed to pass over a portion of the spacer 220. The ligament L, which may also include any other appropriate soft tissue portion, may be provided over the spacer 220 to assist in implantation of the soft tissue. Each of the ridges 226A-226D assist in separating various portions of an implant and also define a major or exterior diameter of the spacer 220. Therefore, the spacer 220 may be used to hold an implant in an implanted position and also may assist in healing after the implantation. Nevertheless, the spacer 220 may be implanted with the anchor 20 in cooperation with the anchor 20 to assist in implanting a selected tissue portion.

Figure 7B:
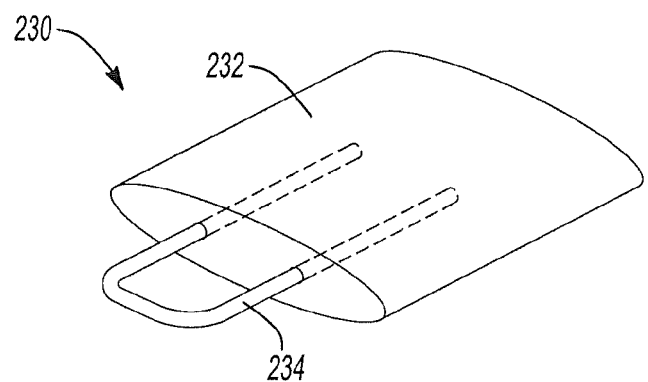

With reference to FIG. 7B, a spacer 230 according to various embodiments is illustrated. The spacer 230 includes a body portion 232 which may include or have extending therefrom an anchor attachment portion 234. The anchor attachment portion 234 may interconnect with the anchor 20, or any appropriate anchor portion, to assist in cooperating with a soft tissue implant to assist in implantation of the implant. As with the spacer 220, the soft tissue implant may be laid over the body portion 232 to assist in holding the soft tissue in a selected implant area and assist in healing after the implantation. It will be understood that the body portion 232 may be formed in any appropriate shape, geometry, size, and other proportions. For example, the body portion 232 may include a geometry or shape to assist in holding the soft tissue relative to a selected region of the body 232 and the implant area.

The attachment region 222 of the spacer 220 and 234 of the spacer 230 may be formed in any appropriate manner. Similarly, the body 224 of the spacer 220 and the body 232 of the spacer 230 may be formed of any appropriate material. For example, the body may be formed of a polymer, metal, or any appropriate biocompatible material. Therefore, the tissue attachment or the attachment region 222 and 234 may be formed of any appropriate material that may interconnect with the material of the body 224 and 232 in an appropriate manner. For example, the attachment area 222 or 234 may be formed of a flexible strand or suture material that may be molded into the body region 224 and 232 of the respective spacers 220 and 230. Alternatively, the attachment portions 232 and 234 may be any other appropriate portion that may be interconnected with the body portions 234 and 232 of the respective anchors 220 and 230. Therefore, the attachment portion 222 and 234 may be welded or otherwise affixed to the body portions 224 and 232.

Figure 7C:
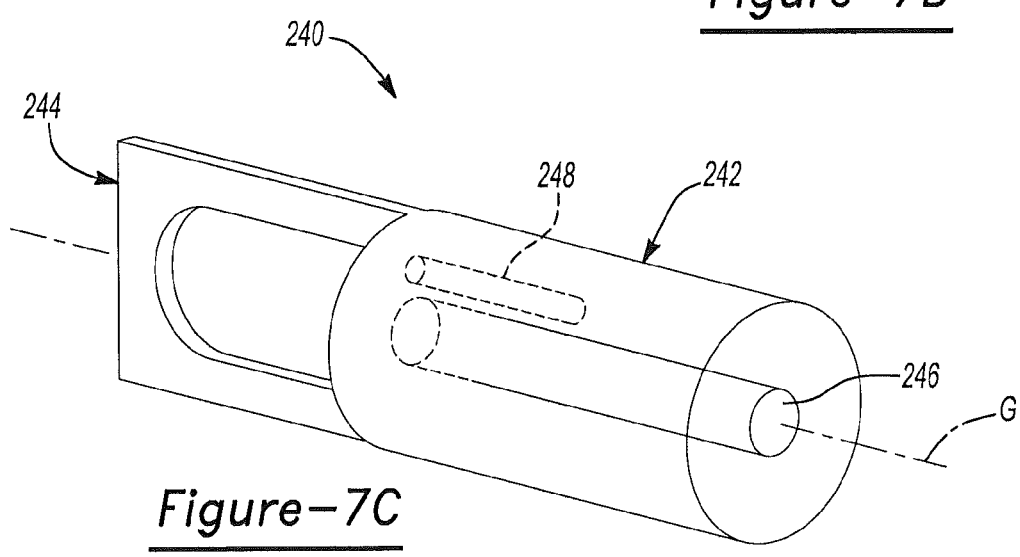

With reference to FIG. 7C, a spacer 240 is illustrated. The spacer 240 may include a body portion 242 from which extends an attachment region 244. The body portion 242 may be formed in any appropriate shape or size, but may be formed as a substantially cylindrical portion extending along an axis G. The body portion 242 may also define a central cannula 246 which extends along the length of the body portion 242 and also substantially along the axis G. The cannula or any other region may be provided for selected purposes, such as allowing for passage of a guide wire or the like.

The attachment region 244 may be affixed to the body region 242 and interconnected therewith in any appropriate manner. For example, the attachment region may be substantially rigid and be formed in generally integrally or as one piece with the body region 242. Therefore, the spacer 240 may be formed a single piece, such as with molding or casting of various materials. Moreover, the spacer 240 may be formed of any appropriate material such as a ceramic, polymer, metal, metal alloy or combinations thereof. The attachment region 244 allows for attachment of the spacer 240 to a selected member such as the anchor 20. Therefore, the anchor 20 may be interconnected with the spacer 240 for assisting in fixation of a selected soft tissue portion. In addition, the body region 242 may define external grooves or recesses 248 that may extend along a length of the body region 242. Selected portions, such as portions of an implant or a suture member, may be fitted into or engage the groove 248 for positioning the spacer 240 or for fixation of the spacer 240.

Figure 8:
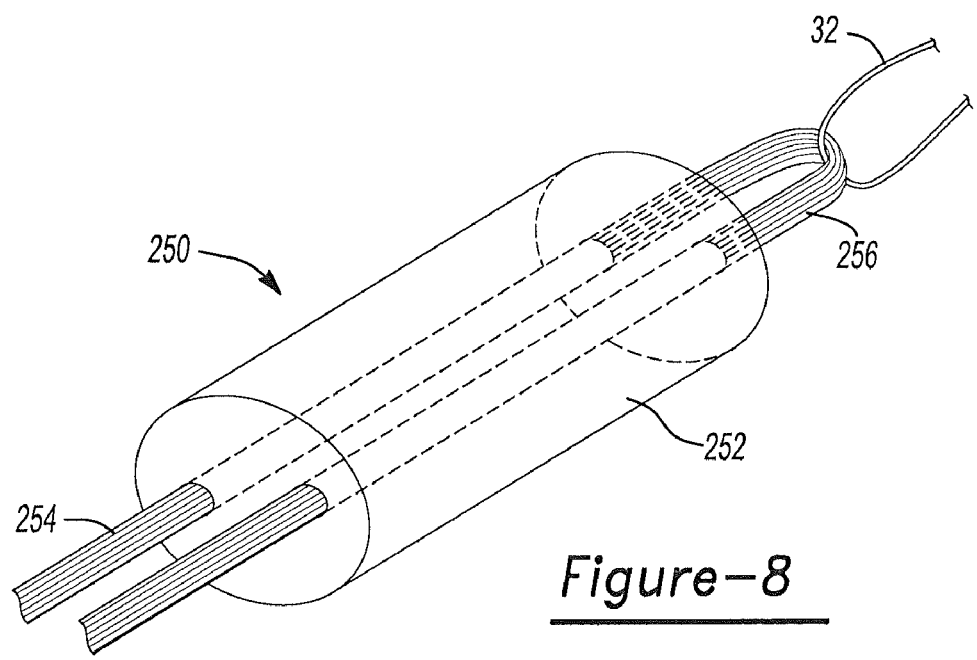
FIG. 8 is a top perspective view of an integrated spacer according to various embodiments.

With reference to FIG. 8, a spacer assembly 250 is illustrated. The spacer assembly 250 includes a block portion or body 252 that may be formed around a selected graft 254. The graft 254 may be any appropriate implant portion such as a tendon or a ligament replacement. The graft 254 portion may define a substantially unitary strand or member that may be formed in the block 252 and interconnected with the connection strand or suture 32 or any other appropriate mechanism. The graft 254 may be looped through the body 252 to form a graft loop 256 at an end of the body 252 opposite the ends of the trailing strand ends of the graft 254.

Figure 8A:
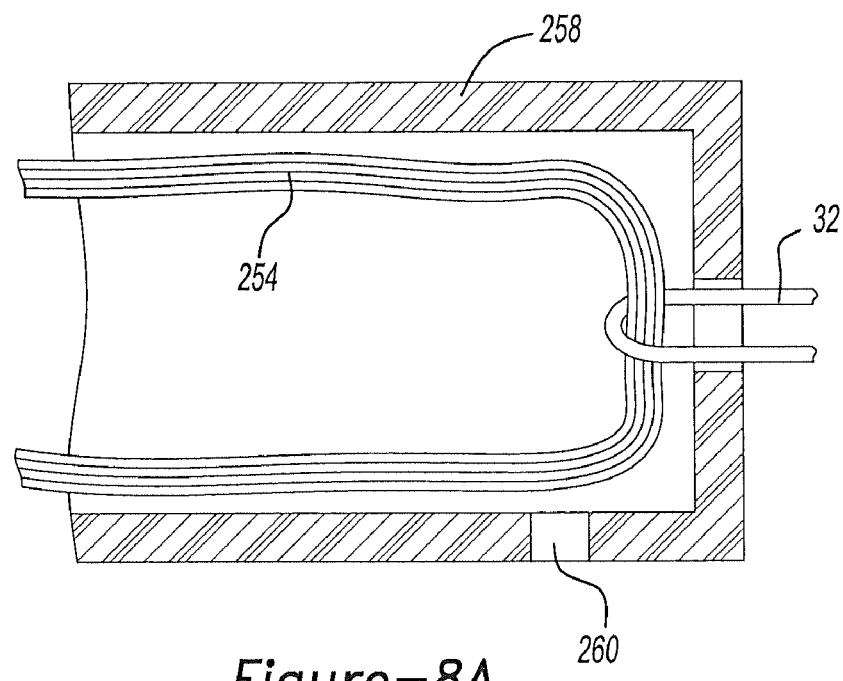
FIG. 8A is a detailed cross-sectional view of a mold to form the spacer.

Although the graft 254 may be formed into the body 252 in any appropriate manner, the graft 254 may be formed into the body 252 by molding a selected moldable material, such as polymer, that may include a bone cement or bio-absorbable polymer, or other materials such as a bone mulch and the like. With reference to FIG. 8A, the graft 254 may be positioned in a selected mold 258. The mold 258 may be formed in any appropriate manner and include an internal geometry or shape defined by a wall of the mold 258 to form the selected body 252. The mold 258 may define a port 260 that allows access to an interior of the mold 258 so that the moldable material may be passed into the interior of the mold 258 to be cured or set up. In this way, the graft 254 may be positioned in the mold and attachment suture 32 or other appropriate portion be interconnected with the graft 254.

After the graft 254 is positioned in the mold 258, the moldable material may be inlet into the mold 258 and allow to cure around the graft 254. The mold 258 may then be appropriately removed from the area to allow interconnection of the graft 254 with a selected portion such as the anchor 20. It will be understood that any appropriate material may be injected into the mold 258 or poured into the mold through any appropriate access port. Also, the mold 258 may be provided either during a procedure or may be preformed depending upon the selected procedure. In addition, the mold 258 may be substantially customized such that a selected area may be appropriately filled with the body 252. Nevertheless, the body 252 may be substantially customized or selectively formed for various procedures to allow for a substantially custom fit for assuring an appropriate positioning of the spacer body 252.

An exemplary method of performing a procedure using the anchor 20 and the spacer 220 is illustrated. It will be understood that although the anchor 20 and the spacer 220 are described as an exemplary way of performing a method of using an anchor or spacer, it will be understood that any appropriate anchor or spacer may be used. In addition, the anchor 20, or any appropriate anchor, may be used alone and not with the spacer 220, or any appropriate spacer. Likewise, the spacer 220, or any appropriate spacer, may be used with any appropriate portion and not with the anchor 20 or any other appropriate anchor. Therefore, it will be understood that the following method described and illustrated as merely exemplary of a method of performing a selected procedure and is not intended to limit the procedure.

Figure 9:
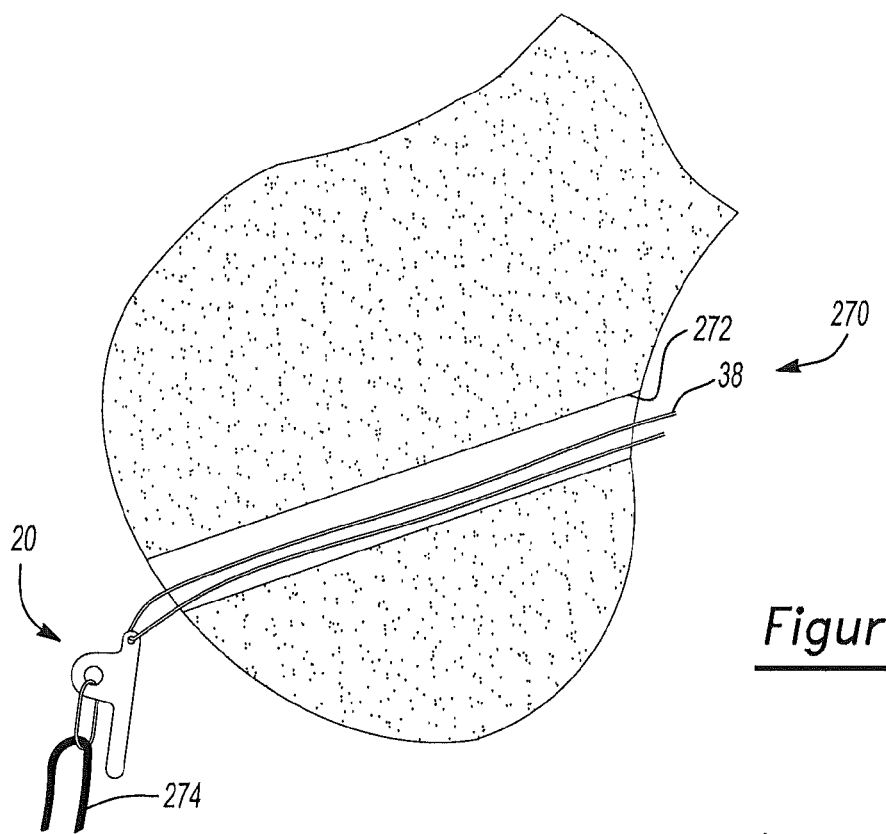
FIG. 9 is an cross-sectional view of a femur exemplary illustrating a soft tissue anchor according to various embodiments in an unimplanted position.

With initial reference to FIG. 9, a procedure may be performed relative to a femur 270 of an anatomy. For example, a bore 272, also known as femoral bore 272, may be formed through a portion of the femur. Although the following description relates generally to the replacement of an anterior curiciate ligament (ACL), it will be understood that the various methods and the instruments may be used for any appropriate procedure in an ACL replacement or reconstruction is merely exemplary. In addition, it will be understood that the ACL graft is generally interconnected with the tibial portion, not particularly illustrated, but generally known in the art. Likewise, the femoral bore 272 may be formed using any appropriate instruments, such as drill or reamer. These are generally known in the art and not described in detail herein.

Nevertheless, once the bore 272 is formed, or at any other time appropriate to the procedure, the anchor 20 may be positioned to be moved through the bore 272. The anchor 20 interconnected with the activation suture 38 may also be interconnected with a graft portion 274. The graft portion 274 may be any appropriate graft portion, such as an allograft or zenograft, that may either be natural or synthetic materials. In addition, the attachment suture 32 is generally provided through the eyelet 30 of the anchor 20. The suture 32 may include a plurality of loops that may be formed from a single strand or a plurality of strands. Nevertheless, the attachment suture 32 may include a plurality of strands of a suture material for various reasons, such as reduced creep and stretching of the suture to further insure appropriate positioning of the graft 274. The graft 274 may be interconnected with the anchor 20 in any appropriate manner. For example, the graft 274 may also be passed simply through the eyelet 30 rather than being interconnected with the attachment suture 32. The graft 274 may be interconnected with the anchor 20 prior to a procedure or inneroperatively. Similarly, the activation suture 38 may be interconnected with the anchor 20 at any appropriate time.

Nevertheless, once the bore 272 is formed through the femur 270, the activation suture may be passed through the bore 272. The activation suture 38 may be passed through the bore 272 in any appropriate manner. For example, a guide wire may be used to assist in forming the bore 272 which may be interconnected with a end of the activation suture 38 to assist in passing the activation suture 38 through the bore 272 of the femur 270. Once the activation suture 38 is passed through the bore 272, the activation suture 38 may be used to assist in passing the anchor 20 through the femoral bore 272.

The activation suture 38 is interconnected with the activation portion 24 of the activation lever 26 of the anchor 20. Therefore, manipulating the activation suture 38 may assist in moving the anchor 20 through the femoral bore 272. The activation suture 38 may be used to urge the anchor 20 into any appropriate position in the femoral bore 272 or through the femoral bore 20.

Figure 10:
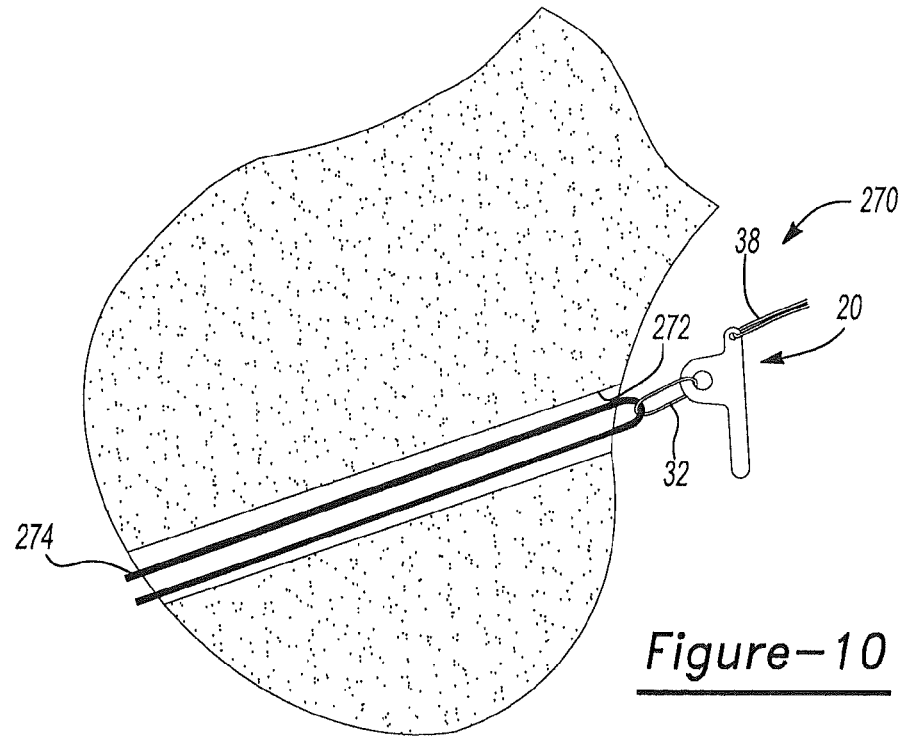
FIG. 10 is a cross-sectional view of a femur exemplary illustrating the soft tissue anchor according to various embodiments in a partially implanted orientation.

With reference to FIG. 10, the anchor 20 may be passed through a substantial portion of the femoral bore 272. The anchor 20 may be passed any appropriate distance through the femoral bore 272, such as a distance great enough to allow the activation lever 26 to be operated. For example, the anchor 20 may be passed a distance through the femoral bore 272 such that a majority of the activation lever 26 is free of the bore 272.

Once the activation lever 26 can be activated, the activation suture 38 may be used to activate the activation lever 26. In activating the activation lever 26, the activation lever 26 is operably moved to an activated position by rotating it a selected distance relative to the femur 270. Shown particularly in phantom in FIG. 10, the activation lever 26 may be moved a distance such that a portion of it extends beyond the edges of the bore 272. This allows the activation lever 26 to engage a selected portion of the femur 270 after the activation lever 26 has been activated.

Figure 11:
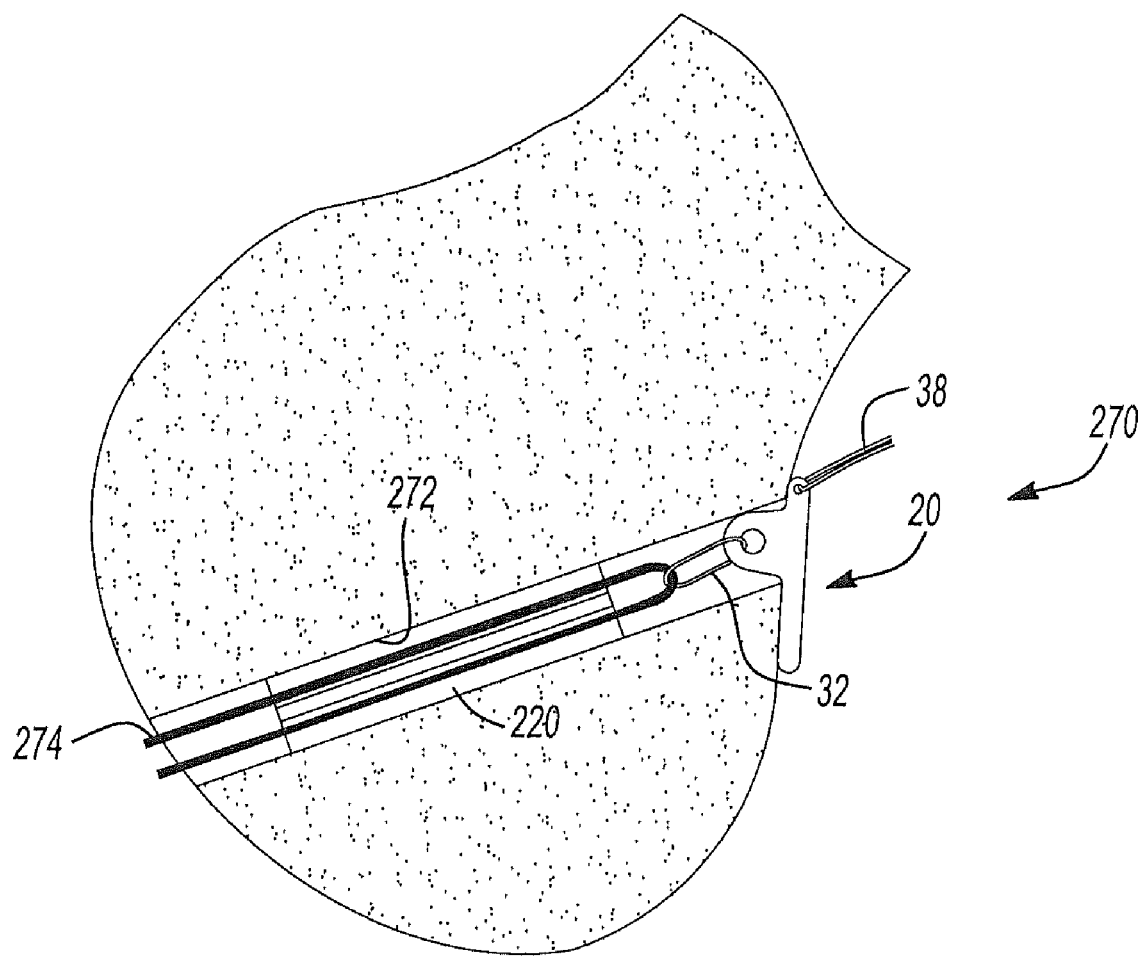
FIG. 11 is a soft tissue anchor according to various embodiments in a substantially implanted position including a spacer.

With reference to FIGS. 10 and 11, once the activation lever 26 has been activated, the graft 274 may be used to set the anchor 20 in position. The anchor 20 may be pulled adjacent to a portion of the femur 270 such that the activation lever 26 is operable to engage a surface 280 of the femur 270. In this way, the activation lever 26 engages the femur 270 such as the anchor 20 is not able to substantially move a distance through the bore 272 after the activation lever 26 has engaged the surface 280 of the femur 270. In this way, the graft 274 may be held within the bore 272 at a selected position due to the interconnection with the anchor 20. The activation lever 26 engages the femur 270 to reduce or substantially eliminate the possibility of the anchor 20 moving back through the femoral tunnel 272.

According to various embodiments, such as the anchor 20 and the spacer 220 illustrated at FIG. 7A, may also engage the graft 274 that is positioned in the femoral tunnel 272. The spacer 220 interconnects with the connection suture 32 through the connection 22. The graft 274 may be looped through the connection suture 32 and over the spacer 220. The spacer 220 may fill a portion of the bore 272 such that the graft 274 may not be allowed to substantially bind on the connection suture 32. For example, the spacer 220 forces apart or holds apart the portions of the graft 274 such that the pressure on the graft 274 may be spread over a greater area rather than at a very small area next to the connection suture 32.

In addition, the spacer 220 may assist in positioning the graft 274 near the wall of the femoral tunnel 272. This may assist in ingrowth of natural tissue into the graft 274 to assist in fixation of the graft 274 in the femoral tunnel 272. In addition, the spacer 220 may be sized to substantially engage a portion of the femoral tunnel 272 such that the bone may grow into the spacer 220. In this way, the spacer 220 may also assist in fixing the graft 274 to a selected position in the femoral tunnel 272. In addition, the spacer 220 may be interconnected with the anchor 20, or any appropriate anchor or assembly according to various embodiments, to at least initially hold the graft 274 at a selected position.

Therefore, it will be understood that any appropriate spacer, such as the spacer 220 may be used with any appropriate anchor, such as the anchor 20, to assist in connecting the graft 274 in the femoral tunnel 272. In addition, the spacer 220 may assist in allowing a long term interconnection of the graft 274 with the femoral tunnel 272 while the anchor 20 may provide the substantially initial and temporary fixation of the graft 274 relative to the femoral tunnel 272. Alternatively, all portions of the connection may be substantially permanent such that the graft 274 may be mechanically fixed relative to the femoral bore 272.

Therefore, it will be understood that the anchor may pass through a portion of a bore, such as the femoral bore 172, to allow for holding a selected soft tissue, such as an ACL graft 174, relative to a selected portion. Although the ACL graft 174 may be fixed relative to the femoral bore 172, it will be understood that any appropriate soft tissue portion may be fixed or held relative to a selected portion with an appropriate anchor. Simply providing the ACL graft is exemplary of various procedures and implants.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A method of fixing a graft in a selected region of an anatomy with an anchor member, comprising:
   forming a bore in the selected region of the anatomy thereby defining an interior surface within the bore and an exterior surface outside of the bore;
   interconnecting a flexible member with a connection region of the anchor member, the flexible member biased in a substantially relaxed position and the anchor member oriented in an activated position;
   attaching the graft to the flexible member;
   passing the anchor member through a selected portion of the bore with the flexible member in a stressed position and the anchor member oriented in a non-activated position;
   moving the anchor member out from within the bore to cause the flexible member to return to the relaxed position, which orients the anchor member in the activated position, and selectively engaging the exterior surface with the anchor member; and
   affixing the graft in a selected position.

2. The method of claim 1, further comprising:
   passing the anchor member through the selected portion of the bore by pulling the anchor member at an activation portion defined by the anchor member.

3. The method of claim 2, wherein the activation portion and the anchor member are integrally formed as a single member.

4. The method of claim 1, further comprising:
   interconnecting an activation member with the anchor member;
   passing the activation member through the bore; and
   moving the anchor member through the bore with the activation member.

5. The method of claim 1, further comprising:
   passing a spacer through a selected portion of the bore relative to the anchor member.

6. The method of claim 5, further comprising:
   connecting the spacer to the flexible member;
   wherein passing the anchor member also passes the spacer through the bore.

7. The method of claim 6, further comprising:
   positioning the graft about a portion of the spacer, such that the graft is held relative to the spacer as the spacer is passed through the bore.

8. The method of claim 1, further comprising:
   engaging a portion of the bore with a spacer.

9. The method of claim 1, further comprising:
   interconnecting a spacer with the anchor member; and
   separating a portion of the graft with the spacer.

10. The method of claim 9, wherein interconnecting a spacer member includes a spacer member having a cross-section defined by at least one of cruciform, a circle, a square, an ellipsoid, or combinations thereof.

11. The method of claim 9, wherein interconnecting a spacer member with the anchor member includes:
    connecting a connection device to the flexible member and the spacer member such that said anchor member is operable to move relative to said spacer member about said flexible member.

12. The method of claim 9, wherein separating a portion of the graft with the spacer includes substantially forming the spacer member around a portion of the graft to hold at least a first portion of the graft from a second portion of the graft.

13. The method of claim 9, wherein separating a portion of the graft with the spacer includes passing at least a portion of the graft through the spacer such that the spacer substantially holds a first portion of the graft a distance from a second portion of the draft.

14. The method of claim 1, wherein interconnecting the flexible member with the anchor member includes interconnecting, a wire, a shape memory material, and combinations thereof with the anchor member.

15. The method of claim 1, wherein interconnecting the flexible member with the anchor member includes interconnecting a shape memory material with the anchor member.

16. The method of claim 1, wherein associating the graft with the flexible member includes substantially associating an ACL graft to replace an anterior cruciate ligament with the flexible member;
    wherein holding the graft in a selected position includes holding the ACL graft relative to at least a portion of the femur.

17. The method of claim 1, further comprising: interconnecting a first flange of the flexible member with a first transverse bore of the connection region and interconnecting a second flange of the flexible member with a second transverse bore of the connection region, the first flange having a first extending portion extending from the first flange and the second flange having a second extending portion extending from the second flange, the first extending portion and the second extending portion are substantially relaxed to retain the anchor in the activated position in which a first plane defined by the first and the second extending portions is non-coplanar with a second plane extending from a first end of the anchor member to a second end of the anchor member that is opposite to the first end; and wherein in the non-activated position the first plane is not perpendicular to the second plane.

18. The method of claim 17, wherein the flexible member includes a curved portion connecting the first extending portion and the second extending portion; and interconnecting the graft with the curved portion.

19. A method of fixing a graft in a selected region of an anatomy with an anchor member, comprising:

attaching the graft to a first flexible member biased in a substantially relaxed position and extending from an engaging portion of the anchor member that is between a first end and a second end of the anchor member, where a longitudinal axis extends between the first end and the second end, and the anchor member is oriented in an activated position;

pulling the anchor through a bore in the selected region using a second flexible member extending from an activation area of the anchor member that is located between the first end and a mid-point of the longitudinal axis, the first flexible member is positioned in a stressed position and the anchor is in a non-activated position as the anchor is pulled such that the longitudinal axis is approximately parallel to an axis of the bore and the first end is pulled through the bore prior to the second end, the first flexible member is biased to revert to the substantially relaxed position to cause the anchor to revert to the activated position after pulling the anchor through the bore such that the longitudinal axis is transverse to the bore; and affixing the graft in the selected region of the anatomy.

20. The method of claim 19, further comprising attaching the first flexible member to the engaging portion of the anchor member by passing at least a portion of the first flexible member through a passage that is offset from the longitudinal axis of the anchor member.

21. The method of claim 19, further comprising attaching the first flexible member to the engaging portion of the anchor member by passing at least a portion of the first flexible member through a passage through which the longitudinal axis of the anchor member extends.

22. The method of claim 19, further comprising attaching the second flexible member to a passageway at the activation area, the passageway having an axis that is perpendicular to the longitudinal axis.

23. The method of claim 19, further comprising attaching the first flexible member to the engaging portion of the anchor member by inserting a first flange of the first flexible member into a first passageway of the engaging portion and inserting a second flange of the first flexible member into a second passageway of the engaging portion that is spaced apart from and parallel to the first passageway of the engaging portion, a first extending portion connects the first flange to a curved portion and a second extending portion connects the second flange to the curved portion.

24. The method of claim 23, further comprising positioning the first flexible member in the substantially relaxed position such that a first plane defined by both the first extending portion and the second extending portion is at least substantially perpendicular to a second plane defined by the first flange and the second flange; and positioning the first flexible member in the stressed position such that the first plane is not perpendicular to the second plane.

25. The method of claim 19, further comprising connecting a spacer member to the first flexible member with a third flexible member such that the spacer is spaced apart from the first flexible member.

26. The method of claim 19, further comprising providing the first flexible member with a shape memory material.

27. A method of fixing a graft in a selected region of an anatomy with an anchor member, comprising:

attaching the graft to a first flexible member including shape memory material biased in a substantially relaxed position, the anchor positioned in an activated position, the first flexible member extends from an engaging portion of the anchor member that is between a first end and a second end of the anchor member, a longitudinal axis extends between the first end and the second end;

connecting a spacer member to the first flexible member with a second flexible member such that the spacer is spaced apart from the first flexible member;

pulling the anchor through a bore in the selected region using a third flexible member extending from an activation area of the anchor member that is located between the first end and a mid-point of the longitudinal axis, the first flexible member is positioned in a stressed position and the anchor is positioned in a non-activated position as the anchor is pulled such that the longitudinal axis is approximately parallel to an axis of the bore and the first end is pulled through the bore prior to the second end, the first flexible member is biased to return to the substantially relaxed position to cause the anchor member to return to the activated position after pulling the anchor through the bore such that the longitudinal axis is transverse to the bore; and affixing the graft in the selected region of the anatomy.

28. The method of claim 27, further comprising attaching the first flexible member to the engaging portion of the anchor member by inserting a first flange of the first flexible member into a first passageway of the engaging portion and inserting a second flange of the first flexible member into a second passageway of the engaging portion that is spaced apart from and parallel to the first passageway of the engaging portion, a first extending portion connects the first flange to a curved portion and a second extending portion connects the second flange to the curved portion.

29. The method of claim 28, further comprising positioning the anchor member in the relaxed position such that a first plane defined by both the first extending portion and the second extending portion is substantially perpendicular to a second plane defined by the first flange and the second flange; and positioning the anchor member in the stressed position such that the first plane is not perpendicular to the second plane.

30. The method of claim 27, further comprising separating the graft into a plurality of different portions and positioning the spacer between each portion to keep the plurality of different portions separated.

* * * * *

UNITED STATES PATENT AND TRADEMARK OFFICE
CERTIFICATE OF CORRECTION

| | |
|---|---|
| PATENT NO. | : 7,967,843 B2 |
| APPLICATION NO. | : 12/401261 |
| DATED | : June 28, 2011 |
| INVENTOR(S) | : Ryan A. Kaiser, Kevin T. Stone and Troy M. Walters |

It is certified that error appears in the above-identified patent and that said Letters Patent is hereby corrected as shown below:

Column 1, line 48, after "insure", delete "that".

Column 1, line 58, "anatomicat" should be --anatomical--.

Column 2, line 38, "extending" should be --extends--.

Column 3, line 8, after "perspective", insert --view--.

Column 3, line 14, after "embodiments", insert --;--.

Column 3, line 15, "FIG. 7A-7C" should be --FIGS. 7A-7C--.

Column 3, line 21, "is an" should be --is a--.

Column 3, line 26, "is an" should be --is a--.

Column 5, line 1, "a activation" should be --an activation--.

Column 5, line 2, "a activation" should be --an activation--.

Column 5, line 18, "bore 64, 66" should be --bores 64, 66--.

Column 5, line 21, "a activation" should be --an activation--.

Column 5, line 22, "a activation" should be --an activation--.

Column 5, line 47, "a activation" should be --an activation--.

Signed and Sealed this
Twenty-seventh Day of September, 2011

David J. Kappos
*Director of the United States Patent and Trademark Office*

Column 5, line 52, "a activation" should be --an activation--.

Column 6, line 7, "bore 96, 98" should be --bores 96, 98--.

Column 7, line 63, "a activation" should be --an activation--.

Column 7, line 66, "a activation" should be --an activation--.

Column 8, line 9, "164A" should be --164a--.

Column 8, line 34, "174B" should be --174b--.

Column 8, line 35, "a activation" should be --an activation--.

Column 9, line 2, "a activation" should be --an activation--.

Column 9, line 10, "198A" should be --198a--.

Column 9, line 11, "198B" should be --198b--.

Column 9, lines 44-45, "226A, 226B, 226C, and 226D" should be --226a, 226b, 226c and 226d--.

Column 9, line 53, "226A-226D" should be --226a-226d--.

Column 11, line 40, "as" should be --is--.

Column 11, line 55, after "as", insert --a--.

Column 11, line 63, "zenograft" should be --xenograft--.

Column 12, line 17, "with a end" should be --with an end--.

Column 14, line 44, claim 13, "draft" should be --graft--.